United States Patent
Dinsmoor et al.

(10) Patent No.: US 11,141,591 B2
(45) Date of Patent: Oct. 12, 2021

(54) STIMULATION AGGRESSOR MANAGEMENT FOR BIOMEDICAL SIGNAL ACQUISITION SYSTEMS

(71) Applicant: Medtronic, Inc., Minneapolis, MN (US)

(72) Inventors: David A. Dinsmoor, North Oaks, MN (US); Scott R. Stanslaski, Shoreview, MN (US); Erik J. Peterson, Fridley, MN (US); Paul R. Mazanec, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 362 days.

(21) Appl. No.: 16/232,492

(22) Filed: Dec. 26, 2018

(65) Prior Publication Data

US 2019/0126046 A1  May 2, 2019

Related U.S. Application Data

(62) Division of application No. 15/236,788, filed on Aug. 15, 2016, now Pat. No. 10,238,876.

(60) Provisional application No. 62/214,763, filed on Sep. 4, 2015.

(51) Int. Cl.
| | |
|---|---|
| *A61N 1/36* | (2006.01) |
| *A61N 1/375* | (2006.01) |
| *A61N 1/378* | (2006.01) |
| *A61N 1/372* | (2006.01) |
| *A61N 1/37* | (2006.01) |

(52) U.S. Cl.
CPC ..... *A61N 1/36125* (2013.01); *A61N 1/36135* (2013.01); *A61N 1/378* (2013.01); *A61N 1/3718* (2013.01); *A61N 1/3756* (2013.01); *A61N 1/37247* (2013.01)

(58) Field of Classification Search
None
See application file for complete search history.

(56) References Cited

U.S. PATENT DOCUMENTS

| | | |
|---|---|---|
| 4,537,200 A | 8/1985 | Widrow |
| 4,742,831 A | 5/1988 | Silvian |
| 7,203,551 B2 | 4/2007 | Houben |
| 8,498,698 B2 | 7/2013 | Donofrio et al. |
| 8,560,060 B2 | 10/2013 | Donofrio et al. |
| 10,238,876 B2 | 3/2019 | Dinsmoor et al. |

(Continued)

FOREIGN PATENT DOCUMENTS

WO  2014043739 A1  3/2014

OTHER PUBLICATIONS

International Search Report and Written Opinion from International Application No. PCT/US2016/048182, dated Nov. 24, 2016, 13 pp.

(Continued)

*Primary Examiner* — Ankit D Tejani
(74) *Attorney, Agent, or Firm* — Shumaker & Sieffert, P.A.

(57) ABSTRACT

Techniques, devices, and systems for isolating, by isolation circuitry connected to a power source, a voltage from the power source, receiving, by sensing circuitry, the isolated voltage, receiving, by the sensing circuitry, a reference voltage from an implantable reference electrode via a reference node, and sensing, by the sensing circuitry, the biomedical signal with two or more implantable sensing electrodes using the isolated voltage with respect to the reference voltage.

16 Claims, 13 Drawing Sheets

(56) References Cited

U.S. PATENT DOCUMENTS

| | | |
|---|---|---|
| 2004/0215279 A1 | 10/2004 | Houben et al. |
| 2009/0082691 A1 | 3/2009 | Denison et al. |
| 2010/0114258 A1 | 5/2010 | Donofrio et al. |
| 2010/0274114 A1 | 10/2010 | Denker et al. |
| 2012/0120684 A1 | 5/2012 | Tol et al. |
| 2014/0025137 A1 | 1/2014 | Meskens |
| 2014/0167518 A1 | 6/2014 | Risher-Kelly et al. |

OTHER PUBLICATIONS

Prosecution History from U.S. Appl. No. 15/236,788, dated Feb. 9, 2018 through Oct. 30, 2018, 59 pp.

STIMULATION AGGRESSOR MANAGEMENT FOR BIOMEDICAL SIGNAL ACQUISITION SYSTEMS

This application is a divisional of U.S. patent application Ser. No. 15/236,788, filed on Aug. 15, 2016, which claims the benefit of U.S. Provisional Application No. 62/214,763, filed Sep. 4, 2015, the entire content of which is incorporated herein by reference.

TECHNICAL FIELD

The disclosure relates to medical therapy systems, and, more particularly, medical therapy systems including sensing circuitry for sensing biomedical signals.

BACKGROUND

A variety of implantable medical devices that deliver electrical stimulation therapy and/or monitor physiological signals have been proposed. Some implantable medical devices may employ one or more elongated electrical leads and/or sensors. Such implantable medical devices may deliver electrical stimulation therapy to the heart, muscle, nerve, brain, stomach, or other organs. In some cases, implantable medical devices deliver electrical stimulation therapy and/or sense physiological signals via one or more electrodes or sensor elements. For example, stimulation electrodes, sensing electrodes or other sensor elements may be included as part of, or carried by, one or more elongated implantable medical leads. Implantable medical leads may be configured to allow electrodes or sensors to be positioned at desired locations for delivery of stimulation or sensing of biomedical signals. For example, electrodes or sensors may be located at a distal portion of a lead. A proximal portion of the lead may be coupled to an implantable medical device housing, which may contain electronic circuitry such as electrical stimulation generation circuitry and/or sensing circuitry.

SUMMARY

In general, the disclosure is directed toward medical therapy systems that deliver electrical stimulation therapy to a patient and sense physiological signals within the patient. In some examples, the medical therapy system may include electrical stimulation circuitry that delivers stimulation therapy to the patient and sensing circuitry that senses biomedical signals within the patient. The stimulation circuitry and the sensing circuitry may be disposed in a common housing and share a common power source. In other examples, the stimulation circuitry and the sensing circuitry may be disposed in separate housings and share a common power source.

The medical therapy system may include isolation circuitry to reduce interference between the stimulation circuitry and the sensing circuitry that share a common power source. In some examples, the isolation circuitry AC couples one or both of the stimulation circuitry and sensing circuitry to the common power source. Electrical isolation provided by the AC coupled power supply may serve to substantially decouple the sensing circuitry from aggressor signals introduced by the electrical stimulation. For example, the isolation circuitry may allow a reference potential of the sensing circuitry to float on whatever common mode potential is generated from the aggressor signals.

In one example, an implantable electrical stimulation device includes a housing, a power source, sensing circuitry, isolation circuitry, stimulation circuitry, and an implantable reference electrode. The sensing circuitry is configured to sense a biomedical signal of a patient via at least two implantable sensing electrodes. The isolation circuitry is connected between the power source and the sensing circuitry and is configured to isolate a voltage received from the power source, and provide the isolated voltage to the sensing circuitry. The stimulation circuitry is configured to deliver electrical stimulation therapy to the patient via at least two implantable stimulation electrodes. The implantable reference electrode connected to the sensing circuitry and is configured to provide a common mode voltage introduced by electrical stimulation therapy to the patient to the sensing circuitry.

In another example, an implantable electrical stimulation device includes a first housing, a second housing, and a third housing. The first housing comprising a power source, a first portion of a first isolation circuitry connected to the power source, and a first portion of a second isolation circuitry connected to the power source. The second housing comprising a second portion of the first isolation circuitry connected to the first portion of the first isolation circuitry, sensing circuitry connected to the first isolation circuitry and configured to sense a biomedical signal via at least two implantable sensing electrodes, and an implantable reference electrode connected to the sensing circuitry and configured to provide a common mode voltage introduced by electrical stimulation therapy to a patient to the sensing circuitry. The third housing comprising a second portion of the second isolation circuitry connected to the first portion of the second isolation circuitry, and stimulation circuitry connected to the second isolation circuitry and configured to deliver electrical stimulation therapy to the patient via at least two stimulation electrodes. The first isolation circuitry is configured to isolate a first voltage received from the power source and provide the isolated first voltage to the sensing circuitry, and the second isolation circuitry is configured to isolate a second voltage received from the power source and provide the isolated second voltage to the stimulation circuitry.

In another example, an implantable electrical stimulation device includes a first housing and a second housing. The first housing comprising a power source, and a first portion of isolation circuitry connected to the power source. The second housing comprising a second portion of the first isolation circuitry connected to the first portion of the first isolation circuitry, a second isolation circuitry connected to the second portion of the first isolation circuitry, sensing circuitry connected to the second isolation circuitry and configured to sense a biomedical signal via at least two implantable sensing electrodes, an implantable reference electrode connected to the sensing circuitry and configured to provide a common mode voltage introduced by electrical stimulation therapy to a patient to the sensing circuitry, and stimulation circuitry connected to the second portion of the first isolation circuitry and configured to deliver electrical stimulation therapy to the patient via at least two stimulation electrodes. The first isolation circuitry is configured to isolate a first voltage received from the power source and provide the isolated first voltage to the stimulation circuitry and the second isolation circuitry. The second isolation circuitry is configured to isolate a second voltage received from the first isolation circuitry and provide the isolated second voltage to the sensing circuitry.

In another example, a method includes isolating, by isolation circuitry connected to a power source, a voltage from the power source, receiving, by sensing circuitry, the isolated voltage from the isolation circuitry, receiving, by the sensing circuitry, a reference voltage from an implantable reference electrode via a reference node, and sensing, by the sensing circuitry, a biomedical signal with two or more implantable sensing electrodes using the isolated voltage with respect to the reference voltage.

In another example, a system includes means for isolating a voltage from the power source, means for receiving the isolated voltage from the isolation circuitry, means for receiving a reference voltage from an implantable reference electrode, and means for sensing a biomedical signal with two or more implantable sensing electrodes using the isolated voltage with respect to the reference voltage.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
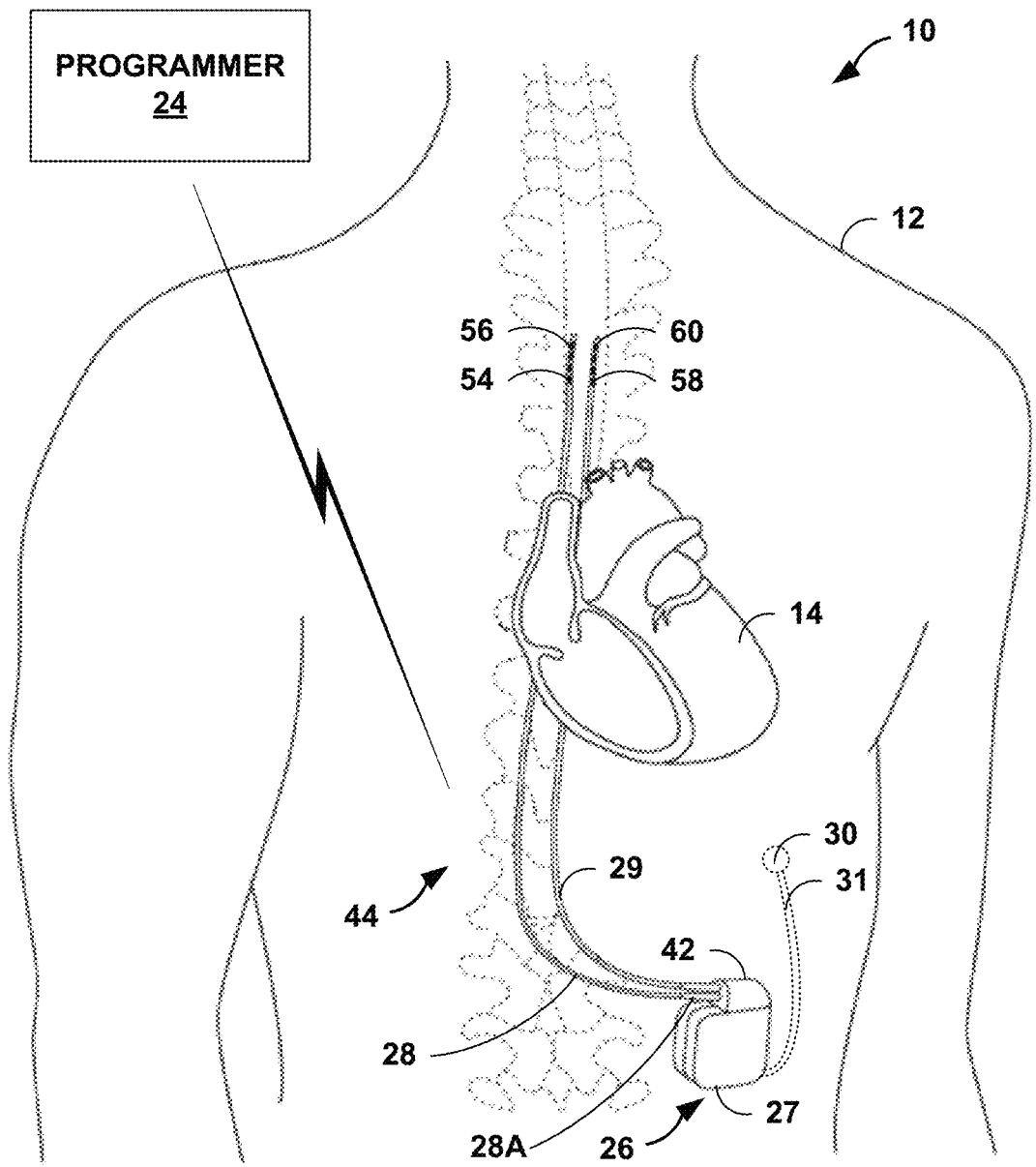
FIG. 1 is a conceptual diagram illustrating an example therapy system that includes an example implantable neurostimulator (INS).

Techniques for minimizing interference between sensing circuitry and stimulation circuitry are described herein. The sensing circuitry and stimulation circuitry may be enclosed in separate housings (e.g., as part of a distributed implantable neurostimulator (INS)) or in a common housing. As described with respect to FIG. 1, in some examples, the INS may comprise an electrical stimulator that provides electrical stimulation therapy to a tissue site. Tissue sites may include any of a variety of organs, nerves, nerve bundles or nerve branches. The target tissue site may include, for example, organs such as the brain, heart, bladder, stomach, or sexual organs, and nerves, nerve bundles and nerve branches such as the spinal cord, gastric nerves, pelvic nerves, and peripheral nerves. In some examples, the target tissue may be a nonmyocardial tissue site (e.g., a tissue site proximate a nerve). A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. The nonmyocardial tissue site may include extravascular tissue sites or intravascular tissue sites.

The stimulation may be gastric stimulation, deep brain stimulation (DBS), pelvic floor stimulation, spinal cord stimulation (SCS) or peripheral nerve stimulation. The stimulation may be configured to address any of a variety of symptoms or disorders such as Parkinson's Disease, essential tremor, or other movement disorders, epilepsy, obsessive compulsive disorder, or other neurological disorders, gastroparesis, obesity, pain, urinary or fecal dysfunction, or sexual dysfunction. Although various examples focus on spinal cord stimulation, the techniques of this disclosure may be applicable to any of a wide variety of different of types of electrical stimulation.

The stimulation circuitry may generate and deliver a stimulation signal to tissue of the patient as part of therapy. The delivery of the stimulation signal by the stimulation circuitry to tissue may cause a common mode potential to occur at implanted electrodes that are electrically connected to sensing circuitry. The common mode potential that is sensed by the sensing circuitry as a result of the delivery of stimulation by the stimulation circuitry may distort or corrupt the target biomedical signals being detected by the sensing circuitry. For example, the common mode potential may distort or corrupt the biomedical signal of interest to the sensing circuitry due to the presence of stimulation signals having amplitudes that may be greater than the amplitudes of target biomedical signals, e.g., by several orders of magnitude.

A simple analogy for understanding the impact of stimulation signals on the sensing of target biomedical signals is seeing the surface of the water from a boat (e.g., sensing a target biomedical signal). If the boat is anchored and there are waves on the surface of the water (e.g., common mode voltages), the surface of the water may be very difficult to see because the boat is anchored and cannot ride the waves (e.g., common mode voltages distort the target biomedical signal). If the boat is not anchored and allowed to float on the waves, the surface of the water may be easier to see because the boat can ride the waves (e.g., common mode voltage do not distort the target biomedical signal). By isolating the ground of the sensing circuitry from the ground of the power source and the stimulation circuitry and receiving a reference voltage comprising common mode voltages from the tissue of a patient, the sensing circuitry may be unanchored and allowed to closely "ride" the waves (e.g., common mode voltages) while sensing the target biomedical signal.

Various techniques are described herein to reduce or eliminate the effect of a common mode potential that is introduced to sensing circuitry, where the common mode potential is at least partially attributable to the delivery of stimulation by stimulation circuitry. The techniques may include the incorporation of isolation circuitry to reduce or eliminate the effect of the common mode potential. For example, to continue the analogy above, with the isolation circuitry, the sensing circuitry may "ride" the same wave as the boat (e.g., the target biomedical signal), which allows the sensing circuitry to reduce or eliminate the distortion caused by the common mode potential in detecting the target biomedical signal. In accordance with the devices, systems, and techniques described herein, the effects of the common mode potential may also be reduced without adversely affecting the desired intensity of electrical stimulation delivered by stimulation circuitry.

FIG. 1 is a conceptual diagram illustrating an example therapy system 10 that includes an example implantable neurostimulator (INS). Therapy system 10 comprises implantable electrical stimulator 26, which is coupled to leads 28 and 29, and optional reference electrode 30 on lead 31. Electrical stimulator 26 may also be referred to as an implantable neurostimulator (INS) 26. INS 26 may be any suitable implantable medical device (IMD) that includes a signal generator that generates electrical stimulation signals that may be delivered to a tissue site within patient 12. Also shown in FIG. 1 are heart 14 and spinal cord 44. Example tissue sites may include tissue sites mentioned above. In the example of FIG. 1, for stimulation of spinal cord 44, leads 28, 29 may be implanted to place electrodes proximate any of a variety of different levels of spinal cord 44.

In the example shown in FIG. 1, the components of INS 26 are enclosed in a common housing. For example, as shown in FIG. 1, the components of INS 26 are enclosed within housing 27. Housing 27 may comprise a hermetically-sealed housing that substantially encloses its components. For example, INS 26 may comprise a hermetically sealed housing that substantially encloses functional components of INS 26, such as sensing circuitry, isolation circuitry, and stimulation circuitry.

Optional reference electrode 30 may work in conjunction with the isolation circuitry to reduce common mode voltages in the sensing of target biomedical signals. In some examples, housing 27 may be used in place of optional reference electrode 30. In other examples, housing 27 may be used with optional reference electrode 30. The components of INS 26 are described below with reference to FIGS. 4 and 5, respectively.

INS 26 may be subcutaneously or submuscularly implanted, for example, in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to a target stimulation site by implantable medical leads 28 and 29, and more particularly, via one or more stimulation electrodes carried by leads 28 and 29. Proximal end 28A of lead 28 may be both electrically and mechanically coupled to connector block 42 of INS 26 either directly or indirectly (e.g., via a lead extension). In particular, conductors disposed in the lead body may electrically connect stimulation electrodes (and sense electrodes, if present) of lead 28 to INS 26. Lead 29 may be connected to INS 26 in a similar manner.

INS 26 may also be referred to as an electrical signal generator. In some examples, leads 28 and 29 may also carry one or more sense electrodes to permit INS 26 to sense electrical signals from the patient, such as near a target stimulation site or elsewhere. Furthermore, in some examples, INS 26 may be coupled to provide stimulation between two or more electrodes on one or more leads, e.g., for bilateral or multi-lateral stimulation or may instead provide unipolar stimulation between an electrode on one of leads 28 and 29 and an electrode on housing of INS 26. In examples where leads 28 and 29 carries one or more sense electrodes, the sense electrodes may be coupled to sensing circuitry within INS 26.

In some examples, INS 26 may also be connected to reference electrode 30. Reference electrode 30 may allow for the sensing circuitry to more closely "ride" on top of the common mode voltage introduced into the body tissue by stimulation from the stimulation circuitry. In some examples, reference electrode 30 may comprise a relatively larger surface area compared to stimulation and sensing electrodes carried by leads 28 and/or 29. Reference electrode 30 may be positioned anywhere within the tissue of patient 12. In some examples, reference electrode 30 may be positioned near one or more sensing electrodes of leads 28 and 29. In some examples, INS 26 may be connected to reference electrode 30 at connector block 42. In other examples, INS 26 may be connected to reference electrode 30 at a connection block separate from connector block 42. In other examples, reference electrode 30 may be carried by one of leads 28, 29.

Proximal end 28A of lead 28 may be both electrically and mechanically coupled to connector block 42 of INS 26 either directly or indirectly (e.g., via a lead extension). Conductors disposed in the lead body of lead 28 may electrically connect stimulation electrodes (and sense electrodes, if present) carried by lead 28 to INS 26. Lead 29 may be connected to INS 26 in a similar manner.

Figure 4:
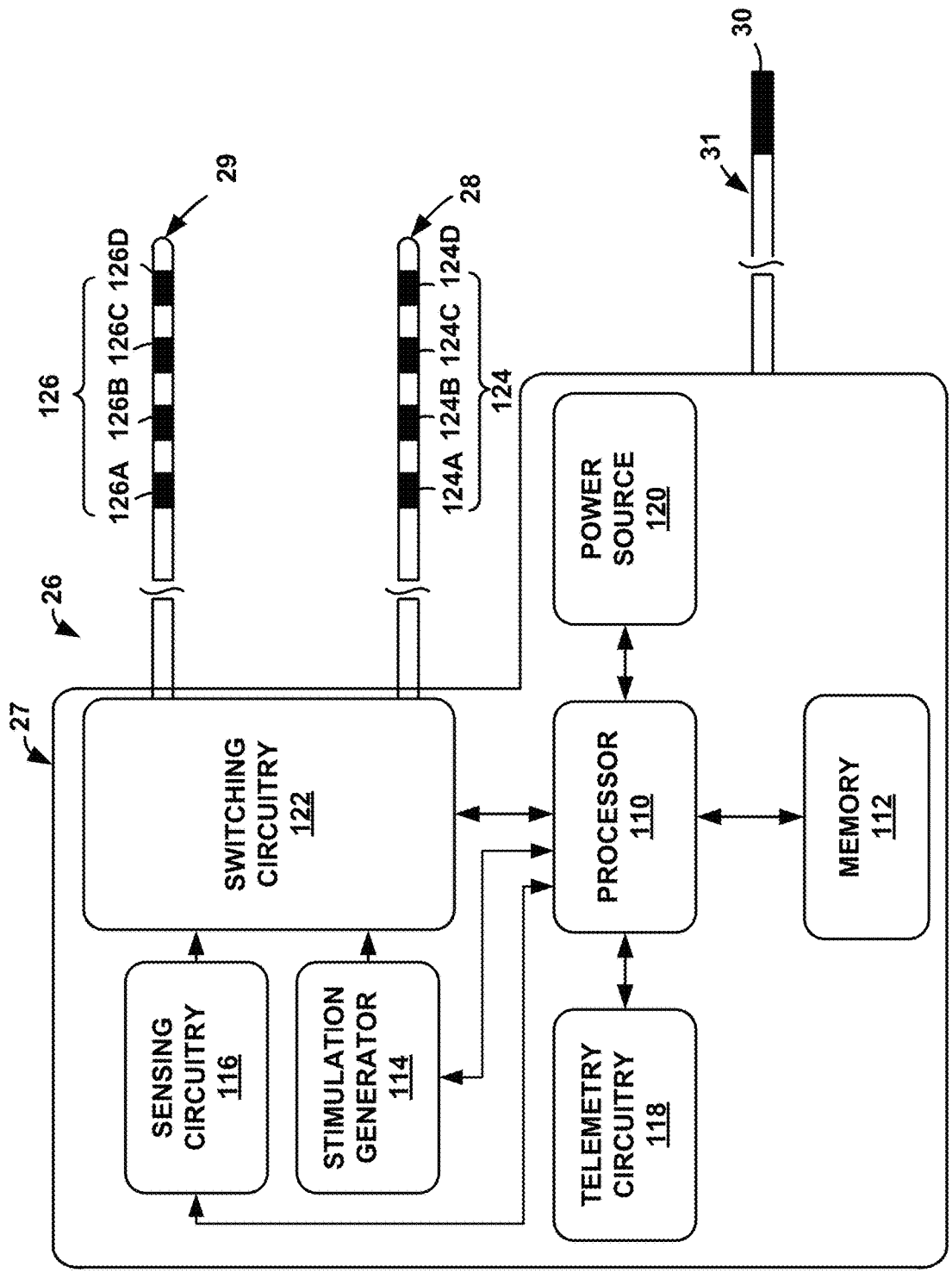
FIG. 4 is a functional block diagram illustrating an example INS that senses physiological signals while generating and delivering electrical stimulation to tissue of a patient.

In the example shown in FIG. 1, INS 26 provides electrical stimulation therapy of spinal cord 44 of patient 12. In other examples, electrodes of lead 28 may be positioned to deliver electrical stimulation to any other suitable nerve, organ, muscle or muscle group in patient 12, which may be selected based on, for example, a therapy regimen selected for a particular patient. The electrical stimulation signals generated and delivered by INS 26 may be referred to as neurostimulation signals. However, in some examples, INS 26 may deliver electrical stimulation to a target tissue site that is not proximate to a nerve. For example, in some examples, INS 26 may deliver electrical stimulation to a peripheral nerve field site, whereby the electrodes of lead 28 (e.g., electrodes 124 or electrodes 126, as shown in FIG. 4) are implanted in a region where patient 12 experiences pain.

As other examples, INS 26 may deliver electrical stimulation to a muscle, muscle group, organ, or other sites that may not be proximate a nerve. Thus, while "neurostimulation" signals are primarily referred to herein, the disclosure is also applicable to examples in which INS 26 delivers electrical stimulation to other sites or than tissue sites proximate a nerve. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve.

Programmer 24 may include a handheld computing device or a computer workstation. In some examples, programmer 24 may comprise an off-the-shelf device, such as a cell phone or other consumer electronic device. Programmer 24 may include a user interface that receives input from a user. The user interface may include, for example, a keypad and a display, which may for example, be a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, trackball, directional pad, or the like, by which a user may interact with the user interface. In some examples, a display of programmer 24 may include a touch screen display, and a user may interact with programmer 24 via the display.

A user, such as a physician, technician, or other clinician, may interact with programmer 24 to communicate with INS 26. For example, the user may interact with programmer 24 to retrieve physiological or diagnostic information from INS 26. A user may also interact with programmer 24 to program INS 26, e.g., select values for operational parameters of INS 26. With the aid of programmer 24 or another computing device, a user may select values for therapy parameters for controlling therapy delivery by INS 26. By selecting values for amplitude, pulse width, and pulse rate, the physician may generate an efficacious therapy for patient 12 that is delivered via the selected electrode subset.

For example, the user may use programmer 24 to retrieve information from INS 26 regarding sensed physiological parameters of patient 12. As another example, the user may use programmer 24 to retrieve information from INS 26 regarding the performance or integrity of INS 26 or other components of system 11, such as leads 28 and 29, or a power source of INS 26.

The user may use programmer 24 to program a therapy progression, select electrodes used to deliver stimulation pulses, select waveforms for the stimulation pulse, or select or configure a detection algorithm for INS 26. The user may also use programmer 24 to program aspects of other therapies provided by INS 26. In some examples, the user may activate certain features of INS 26 by entering a single command via programmer 24, such as depression of a single key or combination of keys of a keypad or a single point-and-select action with a pointing device.

Programmer 24 may communicate with INS 26 via wireless communication. Examples of wireless communication techniques may include, for example, Bluetooth, Near-field communication (NFC), low frequency or RF telemetry, but other techniques also may be used. In some examples, programmer 24 may include a programming head that may be placed proximate to the patient's body near the INS 26 implant sites in order to improve the quality or security of communication between INS 26 and programmer 24.

Each of leads 28 and 29 includes an elongated insulative lead body, which may carry a number of concentric coiled conductors separated from one another by tubular insulative sheaths. Other lead configurations are also contemplated, such as configurations that do not include coiled conductors. In the example of FIG. 1, bipolar electrodes 54 and 56 are located proximate to a distal end of lead 28 and bipolar electrodes 58 and 60 are located proximate to a distal end of lead 29.

In some examples, electrodes 54, 56, 58, and 60 may take the form of ring electrodes. Each of the electrodes 54, 56, 58, and 60 may be electrically coupled to a respective one of the coiled conductors within the lead body of its associated lead 28 and 29, and thereby coupled to respective ones of the electrical contacts on the proximal end of leads 28 and 29. In other examples, electrodes 54, 56, 58, and 60 may include segmented electrodes, pad electrodes, or the like.

Electrodes 54, 56, 58, and 60, in the example of FIG. 1, may sense electrical signals proximate to spinal cord 44. The electrical signals are conducted to sensing circuitry in INS 26 via conductors in the respective leads 28 and 29. INS 26 also may also deliver stimulation pulses via electrodes 54, 56, 58, and 60 to provide therapy to patient 12. In some examples, as illustrated in FIG. 1, INS 26 includes reference electrode 30, which may be formed integrally with an outer surface of hermetically-sealed housing 27 of INS 26 or otherwise coupled to housing 27, e.g., via a lead 31. In some examples, reference electrode 30 may be defined by an uninsulated portion of an outward facing portion of housing 27 of INS 32. Other division between insulated and uninsulated portions of housing 27 may be employed to define two or more reference electrodes 30. In some examples, reference electrode 30 may comprise substantially all of housing 27. Any of the electrodes 54, 56, 58, and 60 may be used for unipolar sensing or delivery of stimulation in combination with reference electrode 30. Electrodes 54, 56, 58, and 60 may be fabricated from any suitable electrically conductive material, such as, but not limited to, platinum, platinum alloy or other materials known to be usable in implantable stimulation and/or sensing electrodes.

Figure 2:
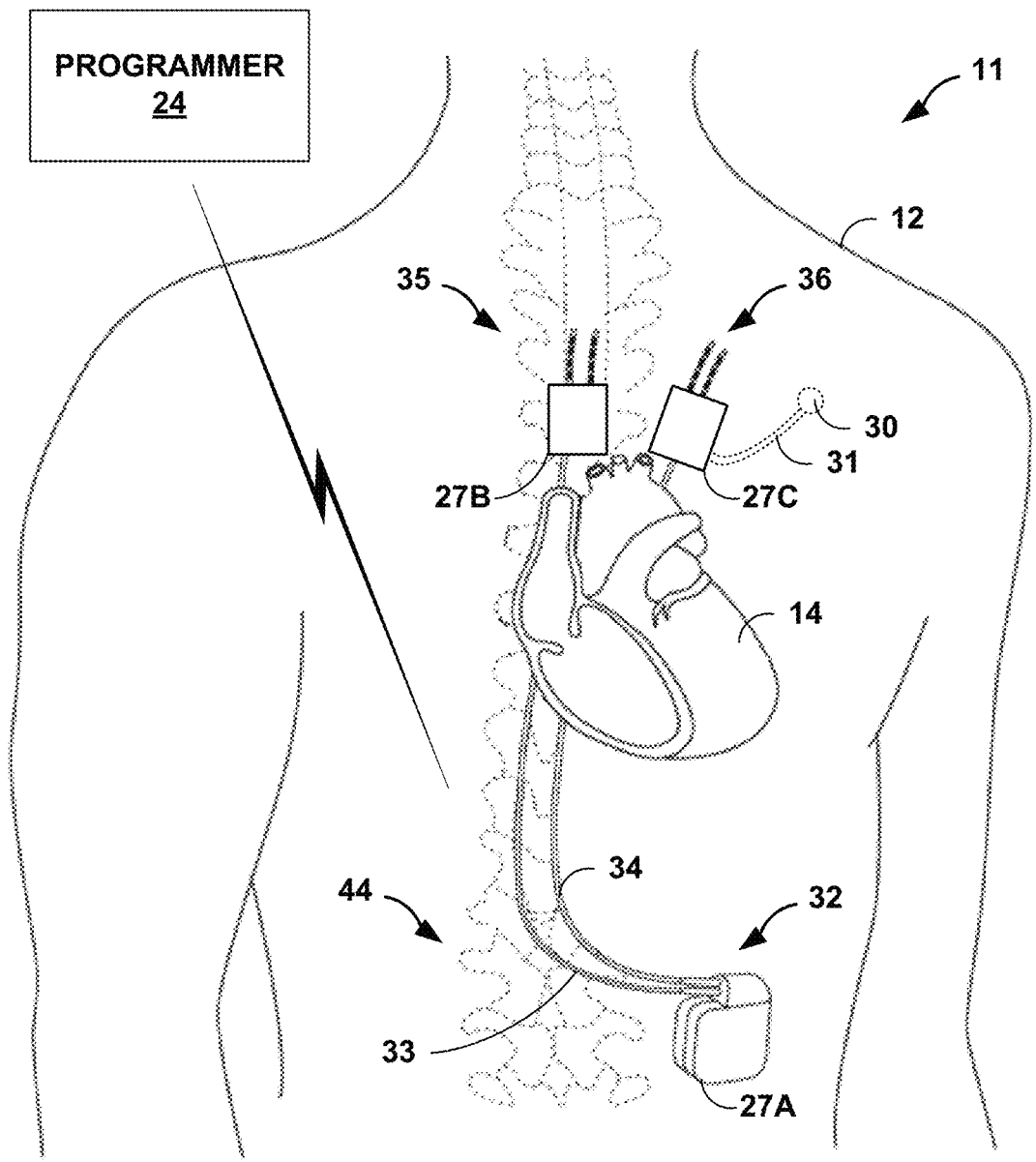
FIG. 2 is a conceptual diagram illustrating an example therapy system that includes an example distributed INS.

FIG. 2 is a conceptual diagram illustrating an example therapy system that includes an example distributed INS 32. INS 32 may be considered to be distributed in the sense that there are separate housings using a single common power source. In the example of FIG. 2, leads 35 and 36 may correspond to leads 28 and 29, respectively, as described in FIG. 1. In some examples, INS 32 may comprise three separate housings 27A-27C, which may correspond to housing 27 as described in FIG. 1. In some examples, housing 27A may include a power source and first portions of first isolation circuitry and second isolation circuitry. First portions of an isolation circuitry include a differential voltage generator, a coupling capacitor, and an optional pull-down resistor as described below. In some examples, housing 27B may include a second portion of the first isolation circuitry connected to the first portion of the first isolation circuitry and stimulation circuitry. In other examples, the stimulation circuitry in housing 27B may be directly connected to the power source in housing 27A with no isolation. Second portions of an isolation circuitry include a coupling capacitor, a rectifier, and a hold capacitor. In some examples, housing 27C may include a second portion of the second isolation circuitry connected to the first portion of the second isolation circuitry, sensing circuitry, and an optional reference electrode 30. The first isolation circuitry and second isolation circuitry isolate at least the sensing circuitry enclosed within housing 27C from the stimulation circuitry enclosed within housing 27B and/or the power source enclosed within housing 27A. The sensing circuitry in housing 27C may be floating with respect to the power source enclosed within housing 27A as described in further detail in FIG. 6.

In the example shown in FIG. 2, in therapy system 11, INS 32 is formed by coupling housing 27A to two separate housings 27B and 27C with conductors 33 and 34 (each containing a plurality of conductors), respectively. In some examples, housing 27B may be positioned to provide stimulation of spinal cord 44 and/or sensing of physiological signals of patient 12. In some examples, housing 27C may be positioned to sense physiological signals of patient 12 and/or provide stimulation of tissue near spinal cord 44 of patient 12. In other examples, housing 27B may deliver stimulation and not provide sensing, and housing 27C may provide sensing but not deliver stimulation. Leads 35 may be introduced into spinal cord 44 in the thoracic region, as shown in FIG. 2. In other examples, leads 35 may be introduced into spinal cord 44 in the cervical or lumbar regions. Leads 36 may be introduced near spinal cord 44. Electrodes of leads 35 and 36 may be positioned within an intrathecal space or epidural space of spinal cord 44, or, in some examples, adjacent nerves that branch off of spinal cord 44. In some examples, housings 27B and/or 27C along with leads 35 and 36 may be implanted in a limb or near a prosthetic limb of patient 12 for electrical stimulation to elicit a motor or sensory response in patient 12.

In examples in which reference electrode 30 is electrically connected to sensing circuitry in housing 27C of INS 32, the common mode voltage introduced by electrical stimulation from electrodes on leads 35 is received at reference electrode 30 and directed to the sensing circuitry that may be enclosed within housing 27C. In examples in which reference electrode 30 is not electrically connected to the sensing circuitry, the common mode voltage introduced by electrical stimulation may be received at housing 27C. In these examples, housing 27C may be used in place of reference electrode 30 and the common mode voltage may be directed to the sensing circuitry. In some examples, the amount of common mode voltage at reference electrode 30 or housing 27C may be used by the sensing circuitry to compensate for the common mode voltage sensed by the sensing circuitry in addition to the target biomedical signal of a physiological signal sensed by the sensing circuitry.

In some examples, INS 32 may delivers electrical stimulation therapy to patient 12 with a current amplitude of about 50 microamps (μA) to about 50 milliamps (mA) (e.g., 3 mA), a pulse duration (i.e., pulse width) of about 10 microseconds (μs) to about 5000 μs (e.g., 50 μs), and a pulse rate (i.e., frequency) of about 1 hertz (Hz) to about 10,000 Hz. However, other stimulation parameter values for INS 32 may be used. For example, rectangular or non-rectangular pulses may be used for stimulation. INS 32 may deliver electrical stimulation to patient 12 substantially continuously or periodically.

In addition, in some examples, INS 32 delivers electrical stimulation to patient 12 based on a sensed physiological condition. The event or physiological condition may be a target biomedical signal that is detected by sensing circuitry of INS 32 or another sensing device. INS 32 may communicate via a telemetry circuitry directly or indirectly (e.g., via an intermediate device, such as programmer 24) using any suitable communication technique. Example communication techniques that may be implemented to facilitate communication between INS 32 and programmer 24 may include, for example, radiofrequency (RF) communication techniques, optical communication techniques, ultrasonic communication techniques, and the like. Communication between INS 32 and programmer 24 may be periodic, e.g., according to a regular schedule, or on an as needed basis. The values for the therapy parameters that define the electrical stimulation delivered by INS 32 may be organized into a group of parameter values referred to as a "therapy program" or "therapy parameter set." "Therapy program" and "therapy parameter set" are used interchangeably herein. In the case of electrical stimulation, the therapy parameters may include an electrode combination, an amplitude, which may be a current or voltage amplitude, and, if INS 32 delivers electrical pulses, a pulse width, and a pulse rate for stimulation signals to be delivered to the patient. An electrode combination may include a selected subset of one or more electrodes of leads 35, as well as leads 36 in the case of therapy system 11 of FIG. 2. The electrode combination may also refer to the polarities of the electrodes in the selected subset. By selecting particular electrode combinations, a clinician may target particular anatomic structures within patient 12. In some cases, INS 32 may deliver stimulation to patient 12 according to a program group that includes more than one therapy program. The stimulation signals according to the different therapy programs in a therapy group may be delivered on a time-interleaved basis or substantially simultaneously.

If INS 32 delivers therapy to patient 12 according to two or more electrode combinations, e.g., according to a therapy program group including two or more therapy programs defining at least two different electrode combinations, time-interleaving the stimulation signals defined each of the therapy programs may result in stimulation that is sequentially applied to different electrodes.

Figure 3:
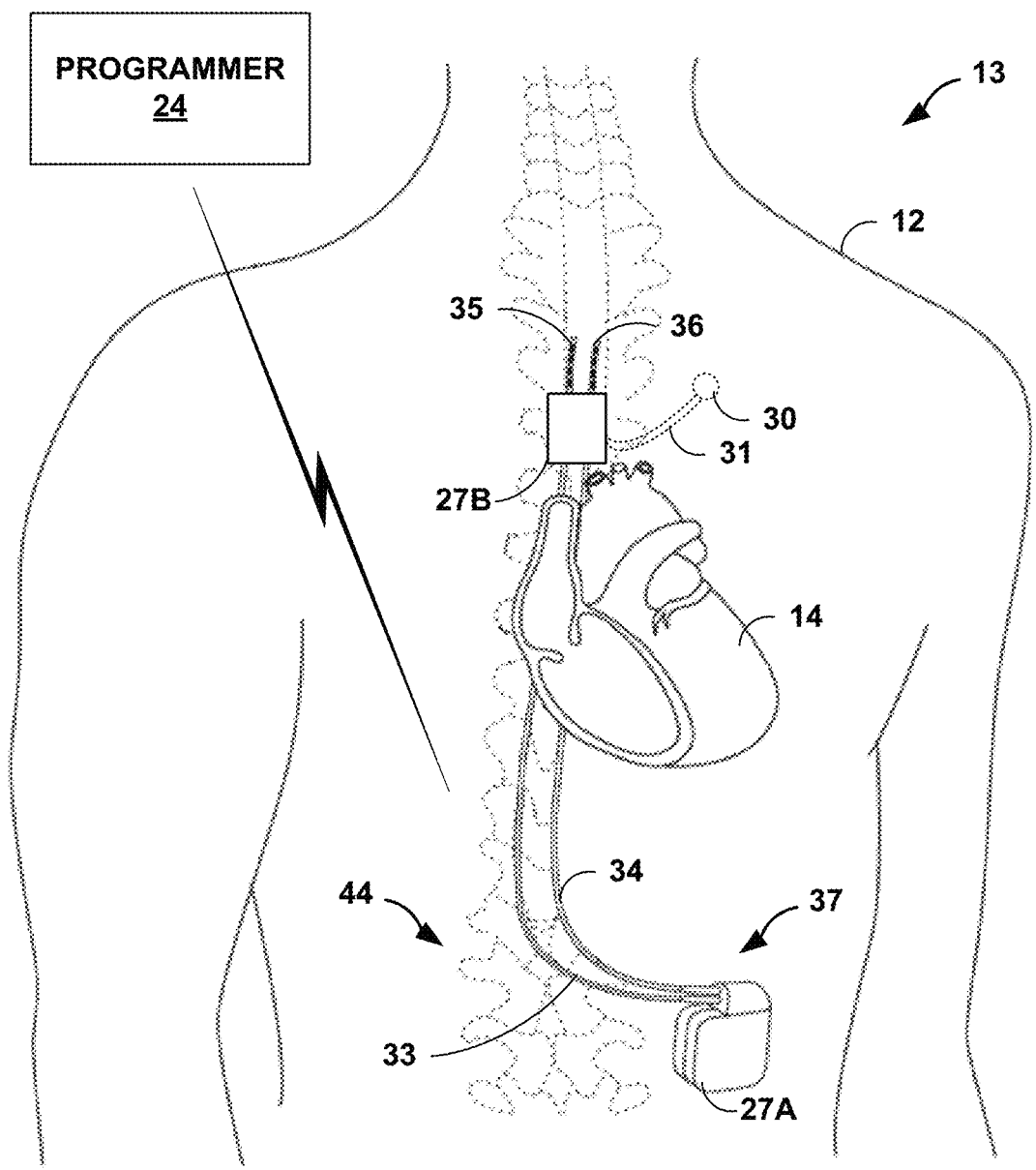
FIG. 3 is a conceptual diagram illustrating an example therapy system that includes another example distributed INS.

FIG. 3 is a conceptual diagram illustrating an example therapy system 13 that includes another example distributed INS 37. In the example of FIG. 3, INS 37, and leads 35 and 36 may correspond to INS 26, and leads 28 and 29, respectively, as described in FIG. 1. In some examples, INS 37 may comprise two separate housings 27A and 27B, which may correspond to housing 27 as described in FIG. 1. In some examples, housing 27A may include a power source and a first portion of isolation circuitry. In some examples, housing 27B may include stimulation circuitry, sensing circuitry, and second portion of the isolation circuitry connected to the first portion of the isolation circuitry, and a second isolation circuitry. In some examples, the second isolation circuitry may provide nested isolation circuitry to further increase the isolation of the power source within housing 27A. In other examples, the stimulation circuitry within housing 27B may be connected with no isolation to the power source in housing 27A and the sensing circuitry within housing 27B may be only connected with isolation to the power source in housing 27A. For example, the stimulation circuitry may be connected to the second portion of isolation circuitry directly In some examples, the isolation circuitry isolates the sensing circuitry from the stimulation circuitry enclosed within housing 27B and/or the power source enclosed within housing 27A. In this way, the sensing circuitry may be floating with respect to the power source enclosed within housing 27A as described in further detail in FIG. 7.

In the example of FIG. 3, in therapy system 13, INS 37 is formed by coupling housing 27A to separate housing 27B with conductors 33 and 34, respectively. In some examples, housing 27B may be positioned to provide stimulation of spinal cord 44 and/or sensing of physiological signals of patient 12. Leads 35 and 36 may be introduced into spinal cord 44 in the thoracic region, as shown in FIGS. 2 and 3. In other examples, leads 35 and 36 may be introduced into spinal cord 44 in the cervical or lumbar regions.

Leads 35 and 36 may be electrically coupled to stimulation circuitry, sensing circuitry, or other circuitry within housing 27B via a connector block. In some examples, proximal ends of leads 35 and 36 may include electrical contacts that electrically couple to respective electrical contacts within the connector block. In addition, in some examples, leads 35 and 36 may be mechanically coupled to the connector block with the aid of set screws, connection pins or another suitable mechanical coupling mechanism. In other examples, leads 35 and 36 may be permanently electrically coupled to stimulation circuitry, sensing circuitry, or other circuitry within housing 27B without a connector block.

FIG. 4 is a functional block diagram of an example INS that senses physiological signals while generating and delivering electrical stimulation to tissue of a patient. FIG. 4 is described with reference to FIG. 1, however, in some examples, FIG. 4 may be described with reference to FIGS. 2 and/or 3. In the example of FIG. 4, INS 26 includes processor 110, memory 112, sensing circuitry 116, stimulation generator 114, switching circuitry 122, telemetry circuitry 118, and power source 120. In the example shown in FIG. 4, processor 110, memory 112, sensing circuitry 116, stimulation generator 114, switching circuitry 122, telemetry circuitry 118, and power source 120 are enclosed within housing 27, which may be, for example, a hermetic housing. In other examples, sensing circuitry 116, stimulation generator 114, and power source 120 may be located in different housings.

Memory 112 includes computer-readable instructions that, when executed by processor 110, cause processor 110 to perform various functions attributed to INS 26 and processor 110 herein. Memory 112 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Stimulation generator 114 generates stimulation signals, which may be pulses as described herein, or continuous time signals, for delivery to patient 12 via selected combinations of electrodes 124. Stimulation generator 114 generates an electrical stimulation signal based on the therapy program parameters. Stimulation generator 114 may be referred to as a signal generator because stimulation generator 114 generates and delivers electrical stimulation signals that provide electrical stimulation. As used herein, the term "stimulation generator" may be interchangeable with the term "signal generator." Processor 110 controls stimulation generator 114 according to stored therapy programs and/or program groups in memory 112 to apply particular stimulation parameter values specified by one or more of programs, such as amplitude, pulse width, and pulse rate.

Processor 110 may include any one or more of a microprocessor, a controller, a digital signal processor (DSP), an application specific integrated circuit (ASIC), a field-programmable gate array (FPGA), or equivalent discrete or integrated logic circuitry. In some examples, processor 110 may include multiple components, such as any combination of one or more microprocessors, one or more controllers, one or more DSPs, one or more ASICs, or one or more FPGAs, as well as other discrete or integrated logic circuitry. The functions attributed to processor 110 herein may be embodied as software, firmware, hardware or any combination thereof. Processor 110 controls stimulation generator 114 to deliver stimulation therapy to spinal cord 44 according to a selected one or more of therapy programs, which may be stored in memory 112. Specifically, processor 110 may control stimulation generator 114 to deliver electrical pulses with the amplitudes, pulse widths, frequency, selected electrodes, and electrode polarities specified by the selected one or more therapy programs.

Processor 110 may also control switching circuitry 122 to apply the stimulation signals generated by stimulation generator 114 to selected combinations of electrodes 124. Switching circuitry 122 is illustrated in FIG. 4, but is optional, and may couple stimulation signals to selected conductors within leads 28 and 29 which, in turn, deliver the stimulation signals across selected electrodes 124 and 126. Switching circuitry 122 may include a switch array, switch matrix, multiplexer, or any other type of switching device suitable to selectively couple stimulation energy to selected electrodes. Hence, stimulation generator 114 is coupled to electrodes 124 and 126 via switching circuitry 122 and conductors within leads 28 and 29. In some examples, INS 26 does not include switching circuitry 122, such that each stimulation electrode is directly connected to either a voltage or current source and each sense electrode is directly connected to a sensing channel of sensing circuitry 116.

Stimulation generator 114 may be a single or multi-channel stimulation generator. In particular, stimulation generator 114 may be capable of delivering a single stimulation pulse, multiple stimulation pulses, or a continuous signal at a given time via a single electrode combination or multiple stimulation pulses at a given time via multiple electrode combinations. In some examples, however, stimulation generator 114 and switching circuitry 122 may be configured to deliver multiple channels on a time-interleaved basis. In this case, switching circuitry 122 serves to time division multiplex the output of stimulation generator 114 across different electrode combinations at different times to deliver multiple programs or channels of stimulation energy to patient 12.

As shown in FIG. 4, stimulation generator 114 may be electrically coupled to leads 28 and 29 either directly or indirectly (e.g., via a lead extension). In the example illustrated in FIG. 4, lead 28 includes electrodes 124A-124D (collectively referred to as "electrodes 124"). Lead 29 includes electrodes 126A-126D (collectively referred to as "electrodes 126"). In some examples, electrodes 124 and 126 may correspond to electrodes 54, 56, 58, and 60 as described in FIG. 1. Stimulation generator 114 may be electrically coupled to electrodes 124 and 126, e.g., via conductors of the respective lead 28 and 29 or, in the case of reference electrode 30, via an electrical conductor disposed within housing 27 of INS 26. Stimulation generator 114 is configured to generate and deliver therapy to spinal cord 44. For example, stimulation generator 114 may deliver electrical stimulation pulses to spinal cord 44 via at least two electrodes from electrodes 124 and 126.

In some examples, processor 110 may use switch circuitry 122 to select, e.g., via a data/address bus, which of the available electrodes are used to deliver stimulation pulses. The switch circuitry may include a switch array, switch matrix, multiplexer, or any other type of switching device suitable to selectively couple stimulation energy to selected electrodes. In other examples, however, stimulation generator 114 may independently deliver stimulation to electrodes 124 and 126, or selectively sense via one or more of electrodes 124 and 126 without switching circuitry 122.

Sensing circuitry 116 monitors signals from at least one of electrodes 124 and 126 in order to monitor electrical activity of spinal cord 44. Sensing circuitry 116 may use switching circuitry 122 to select a particular subset of available electrodes to sense physiological signals. In some examples, processor 110 may select the electrodes that function as sense electrodes via switching circuitry 122, e.g., by providing signals via a data/address bus. In some examples, sensing circuitry 116 includes one or more sensing channels, each of which may comprise an amplifier. In response to the signals from processor 110, switching circuitry 122 may couple the outputs from the selected electrodes to one of the sensing channels of sensing circuitry 116. In some examples, INS 26 does not include switching circuitry 122, such that each sense electrode is directly connected to a sensing channel of sensing circuitry 116.

Telemetry circuitry 118 includes any suitable hardware, firmware, software or any combination thereof for communicating with another device, such as programmer 24 (FIG. 1). Under the control of processor 110, telemetry circuitry 118 may receive downlink telemetry from and send uplink telemetry to programmer 24 with the aid of an antenna, which may be internal and/or external. Processor 110 may provide the data to be uplinked to programmer 24 and the control signals for the telemetry circuitry within telemetry circuitry 118, e.g., via an address/data bus. In some examples, telemetry circuitry 118 may provide received data to processor 110 via a multiplexer.

In some examples, the various components of INS 26 with the exception of sensing circuitry 116 may be directly coupled to power source 120, which may include a rechargeable or non-rechargeable battery. A non-rechargeable battery may be selected to last for several years, while a rechargeable battery may be inductively charged from an external device, e.g., on a daily or weekly basis. In some examples, sensing circuitry 116 may be electrically isolated from power source 120. In this way, sensing circuitry 116 may not share a ground potential with power source 120. For example, the reference voltage as described herein may be different than the ground potential of power source 120. In this example, the reference voltage may be the potential at a reference electrode implanted outside housing 27 and in the tissue of a patient, such as patient 12. In other examples, both sensing circuitry 96 and stimulation generator 94 (e.g., stimulation circuitry) may be isolated from power source 120 and from each other. In this way, both sensing circuitry 116 may not share a ground potential with power source 120 or each other. For example, the reference voltage as described herein may be different than the ground potential of power source 120 and stimulation generator 114.

Electrodes 124 and 126 may comprise ring electrodes. In other examples, electrodes 124 and 126 may be arranged in a complex electrode array that includes multiple non-contiguous electrodes at different angular positions about the outer circumference of leads 28 and 29, as well as different levels of electrodes spaced along a longitudinal axis of leads 28 and 29. The configuration, type, and number of electrodes 124 and 126 illustrated in FIG. 4 are merely one example. In other examples, INS 26 may be coupled to any suitable number of leads with any suitable number and configuration of electrodes. Moreover, leads 28 and 29 may comprise a shape other than a cylindrical shape. As an example, leads 28 and 29 may comprise a paddle-shaped portion that carries electrodes 124. In some examples, housing 27 of INS 26 may also include one or more electrodes.

In the example shown in FIG. 4, lead 31 electrically connects reference electrode 30 to housing 27 of INS 26. Housing 27 may or may not be electrically coupled to stimulation generator 114 or other components shown in FIG. 4. For example, sensing circuitry 116 may be connected to reference electrode 30 via housing 27. In some examples, reference electrode 30 may have a larger conductive surface area than that of any of the electrodes 124 and 126, or the combination of the conductive surface areas of electrodes 124 and 126. In some examples, though not shown in FIG. 4, rather than one electrode, lead 31 may comprise a plurality of similar electrodes that together form reference electrode 30. The plurality of electrodes may be connected to housing 27 via lead 31. For example, each of the plurality of electrodes may be connected to one another via a wire within lead 31, and the wire may be connected to housing 27. In some examples, reference electrode may be directly connected to sensing circuitry 116.

Reference electrode 30 may comprise a ring electrode, coil electrode, patch electrode, pad electrode or any other suitable type of electrode. In some examples, the surface area of reference electrode 30 may be ten, fifty, or greater than one hundred times larger than the surface area of each of electrodes 124. That is, the ratio of the surface area of reference electrode 30 to each of electrodes 124 and 126 may be at least ten, although other ratio values are possible.

As shown in FIG. 4, reference electrode 30 is not electrically connected to any stimulation or sensing circuitry of INS 26. However, in some examples, reference electrode 30 may be electrically connected to sensing circuitry 116. In other examples, leads 28 or 29 may include reference electrode 30, and a conductor within the respective lead 28, 29 may electrically connect reference electrode 30 to housing 27 of INS 26 or sensing circuitry 116.

In some examples, the delivery of stimulation to spinal cord 44 of patient 12 by INS 26 may generate a common mode voltage in the patient's body. This common mode voltage may occur at electrodes 30, 124, and 126. Due to the relatively large conductive surface area of reference electrode 30 with respect to individual electrodes 124 and 126, reference electrode 30 may reduce the DC and AC components of the impedance from the body to the reference node connected to sensing circuitry 116. In some examples, reference electrode 30 may have a surface area of 1 $cm^2$ compared to electrodes 124 and 126 that may each have a surface area of 6 $mm^2$. In some examples, reference electrode 30 may have a surface area of 25 $mm^2$ compared to electrodes 124 and 126 that may each have a surface area of 0.42 $mm^2$.

The reduced impedance at the reference node in conjunction with the isolation of power source 120 provided by the isolation circuitry, allows sensing circuitry 116 to more closely "ride" on top of the common mode voltage introduced into the body tissue by the stimulation. As a result of the reduced impedance, a lower root mean square (RMS) noise floor may be achieved as a function of frequency along with the ability to better resolve small amplitude target biomedical signals in the presence of large common mode voltage in sensed physiological signals.

Figure 5:
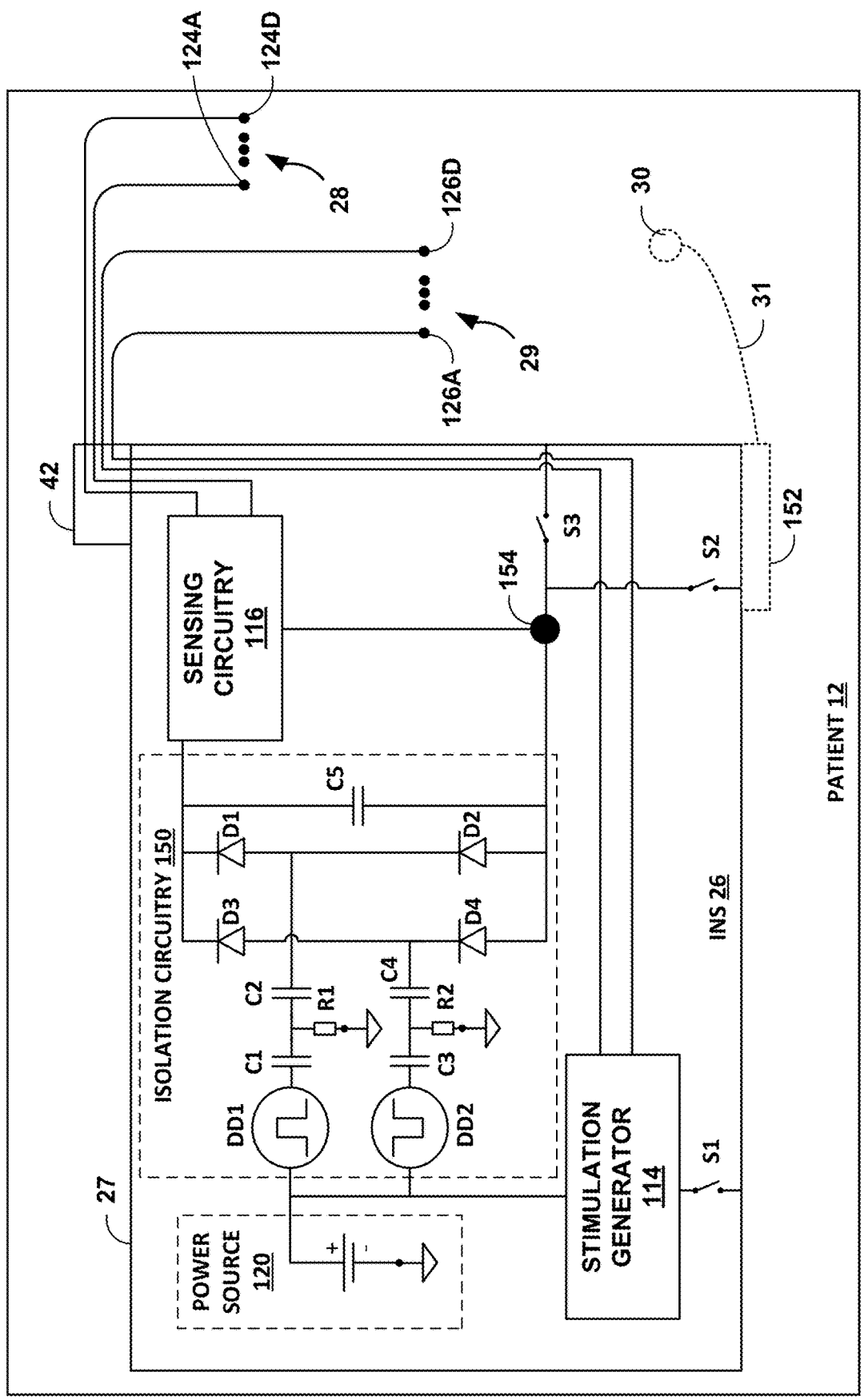
FIG. 5 is a functional block diagram illustrating an example INS of FIG. 1 that senses physiological signals while generating and delivering electrical stimulation to tissue of a patient.

FIG. 5 is a functional block diagram of an example INS 26 of FIG. 1 that senses physiological signals while generating and delivering electrical stimulation to tissue of a patient. FIG. 5 is described with reference to FIGS. 1 and 4. For example, INS 26 includes housing 27, reference electrode 30, lead 31, connector block 42, stimulation generator 114, sensing circuitry 116, power source 120, and electrodes 124 and 126 as described in FIG. 4. Additionally, in the example of FIG. 5, INS 26 includes isolation circuitry 150, connector block 152, and reference node 154.

As illustrated in FIG. 5, housing 27 of INS 26 encloses power source 120, stimulation generator 114, sensing circuitry 116, isolation circuitry 150, and reference node 154. In some examples, housing 27 may also have a second connector block 152 which connects lead 31 comprising reference electrode 30 to reference node 154. In some examples, connector block 152 may be similar to connector block 42 as described in FIG. 1.

Sensing circuitry 116 detects a target biomedical signal via at least two implantable sensing electrodes (e.g., 124A and 124D). Isolation circuitry 150 is connected between power source 120 and sensing circuitry 116. Isolation circuitry 150 isolates a voltage received from power source 120 and supplies the isolated voltage to sensing circuitry 116. In this manner, isolation circuitry 150 operates as a floating power supply to sensing circuitry 116.

Stimulation generator 114 (e.g., stimulation circuitry) delivers electrical stimulation therapy to patient 12 via at least two implantable stimulation electrodes (e.g., electrodes 126A and 126D), which may be carried one or more leads, such as lead 29. In some examples, the stimulation delivered by stimulation generator 114 may introduce a common mode potential in the tissue of patient 12, which may be received at an implantable reference electrode. In some examples, stimulation generator 114 may use housing 27 as a stimulation electrode or return electrode via switch S1. In some examples, housing 27 may be connected to a potential defined by stimulation generator 114. In some examples, switch S1 may not be used, but instead there may be a direct connection between stimulation generator 114 and housing 27.

Implantable reference electrode (e.g., housing 27 and/or reference electrode 30) is connected to sensing circuitry 116 and provides a common mode voltage introduced by electrical stimulation therapy to patient 12 which serves as a reference to sensing circuitry 116. In some examples, reference electrode 30 may be connected to sensing circuitry 116 via lead 31, connector block 152, switch S2, and reference node 154. Reference node 154 raises the reference potential of the floating sensing circuitry to the potential of the tissue (as influenced by the stimulation energy) so that anything sensed by the sensing circuitry floats on top of that reference voltage. Reference node 154 also floats with the actual potential of the tissue patient 12, whether stimulation is being applied or not being applied.

In other examples, implantable reference electrode may be housing 27 and may be connected to sensing circuitry 116 via switch S3 and reference node 154. In yet other examples, to further increase the surface area size of the implantable reference electrode, the implantable reference electrode may be both reference electrode 30 and housing 27 and connected to sensing circuitry 116 via switches S2 and S3 and reference node 154. In some examples, switches S2 and S3 may not be used, but instead there may be a direct connection between sensing circuitry 116 and reference node 154.

Sensing circuitry 116 does not share a ground potential with power source 120 and stimulation generator 114 because of isolation circuitry 150. Instead, sensing circuitry 116 uses a reference voltage provided by reference electrode 30 as the lowest potential. Using this reference voltage as the lowest potential permits sensing circuitry 116 to cancel out of the effect of the common mode voltage in the inputs of sensing circuitry 116, which reduces the distortion and corruption of the sensed biomedical signal. In some examples, sensing circuitry 116 may sense physiological signals with spectral content having a frequency between approximately one hertz (Hz) and approximately five hundred Hz or greater. In some examples, switches S1-S3 may be controlled by processor 110 as described in FIG. 4. In some examples, switches may not be used, but instead there may be a direct connection between the different components and housing 27.

Isolation circuitry 150 is connected between power source 102 and sensing circuitry 116 and provides AC coupling of power source 120 to sensing circuitry 116. Isolation circuitry 150 may include a first differential voltage generator DD1 that is powered by power source 120 and drives one or more first coupling capacitors C1 and C2 with an alternating current waveform, second differential voltage generator DD2 that is powered by power source 120 and drives one or more second coupling capacitors C3 and C4 with an alternating current waveform, a rectifier formed by diodes D1-D4 that rectifies a voltage from the one or more first and second coupling capacitors C1-C4, and a hold capacitor C5 that receives the rectified voltage from the rectifier and provides the rectified voltage as an isolated DC supply voltage for sensing circuitry 116. In some examples, first and second differential drivers DD1 and DD2 may drive a clock signal and its complement, each on a separate conductor. In other examples, a digital data signal may be driven differentially by first and second differential drivers DD1 and DD2 provided the digital data signal has a 50% average duty cycle (e.g., Manchester encoded) and was transmitted at a sufficient rate. In some examples, first and second differential voltage generators DD1 and DD2 may be a CMOS totem-pole output stage, a class AB driver, or any other suitable differential voltage generator. In some examples, bias pull-down resistors connected to the same ground as power source 120 may be between coupling capacitors C1 and C2, and C3 and C4.

In some examples, first differential voltage generator DD1 may produce a fifty percent duty cycle square wave with a five volt amplitude, and second differential voltage generator DD2 may produce a fifty percent duty cycle square wave with the opposite polarity of the square wave output by first differential voltage generator DD1. In these examples, the square wave produced by each of first and second differential voltage generators DD1 and DD2 may have a frequency of approximately two hundred kilohertz (kHz). In some examples, first and second differential voltage generators DD1 and DD2 may produce a waveform other than a square wave, such as a sine wave or any other suitable waveform for power transfer.

In some examples, the rectifier formed by electrodes D1-D4 may be at least one of a full-wave rectifier, a synchronous rectifier, or a half-wave rectifier. In some examples, the rectifier may comprise reference node 154, which is at the lowest potential of the rectifier. In some examples, reference node 154 may be connected to housing 27 by switch S3. In other examples, reference node 154 may be connected to reference electrode 30 by switch S2, connector block 152, and lead 31. In yet other examples, reference node 154 may be connected to both housing 27 and reference electrode 30. In some examples, reference electrode 30 may provide the common mode voltage introduced by electrical stimulation therapy to patient 12 to sensing circuitry 116 and/or isolation circuitry 150. Isolation circuitry 150 may further include hold capacitor C5, which may be configured to power sensing circuitry 116 with respect to a voltage at reference node 154, which may be provided by reference electrode 30.

In some examples, first and second one or more coupling capacitors C1-C4 each may include two coupling capacitors connected in series with each other (e.g., C1 and C2, and C3 and C4). In these examples, a bias pull-down resistor R1 and R2 may be connected between the two coupling capacitors (e.g., C1 and C2, and C3 and C4) and to the same ground as power source 120. In some examples, each of the coupling capacitors (e.g., C1 and C2, and C3 and C4) may have a capacitance of approximately one hundred nanofarads (nF). In some examples, alternatively, isolation circuitry 150 may comprise a DC-to-AC transformer that converts a DC voltage to an AC voltage, a rectifier that rectifies the AC voltage from the DC-to-AC transformer to DC voltage, and a hold capacitor that receives the rectified DC voltage from the rectifier.

As illustrated in FIG. 5, there is no need for isolation between stimulation generator 114 and power source 120. However, in other examples, INS 26 may include second isolation circuitry (not shown) connected between power source 120 and stimulation generator 114, wherein the second isolation circuitry isolates a voltage received from power source 120 and provides the isolated voltage to stimulation generator 114. In some examples, the second isolation circuitry may comprise a third differential voltage generator configured to drive one or more third coupling capacitors, a fourth differential voltage generator configured to drive one or more fourth coupling capacitors, a rectifier configured to rectify a voltage from the one or more third and fourth coupling capacitors, and a hold capacitor configured to receive the rectified voltage from the rectifier. In these examples, the third differential voltage generator may produce an approximately fifty percent duty cycle square wave with an approximately five volt amplitude, and the fourth differential voltage generator may produce the opposite polarity of the third differential voltage generator.

Biomedical signal acquisition systems may be used by clinicians, scientists and engineers to characterize very low amplitude electrical activity, such as local field potentials and evoked potentials in living organisms. However, these signal acquisition systems do not easily manage aggressors (e.g., common mode voltages introduced by electrical stimulation), which are part of a sensed physiological signal and corrupt the desired or target biomedical signal. The corruption is challenging in implanted medical devices because of limited battery capacity that reduces the ability to support aggressor management circuitry and algorithms.

One of the most potent aggressors may be a stimulation signal deliberately applied to the living organism. This stimulation signal may be used to manage a disease state of the living organism. For example, the stimulation signal may be stimulation in the sub-thalamic nucleus to control epilepsy or the stimulation signal may be used to provide diagnostic insight into the integrity of a nerve, as with a somatosensory evoked potential study. In many cases, a biomedical signal of interest or target biomedical signal may occur concurrently with the stimulation pulse or at some interval shortly after the stimulation pulse. The techniques, devices, and systems as described herein may capture these microvolt level signals in the presence of multi-volt stimulation aggressors, e.g., with the aid of isolation circuitry as described in this disclosure. For example, the target biomedical signal may have an amplitude of about 100 nanovolts (nV) to about 300 microvolts (µV).

Some conventional methods employed to ameliorate aggressors include extensive filtering networks, very high common-mode rejection ratios (CMRR) and noise cancelling feedback systems wherein the body is actively driven with the antiphase of the aggressor. Other methods include completely separate power sources for the sensing circuitry and for the stimulation circuitry.

However, these aforementioned approaches require the added burden of managing multiple batteries, loss of intended signal in the filtering network, physically unrealizable CMRR's and excessive power consumption. Additionally, the aforementioned approaches are complex and may increase costs in both parts and design. As described herein, techniques, devices, and systems may permit only power source 120 and one or both of the biomedical sensing circuitry 116 or stimulation generator 114 to be AC coupled from the common power source 120. The isolation afforded by the AC coupled power source serves to largely decouple sensing circuitry 116 from the aggressors introduced by electrostimulation delivered by stimulation generator 114, as isolation and derivation of the reference voltage of sensing circuitry 116 from reference node 154 is allowed to float on whatever common mode potential results from the aggressors. In some examples, the isolation may be provided via a transformer. In other examples, the isolated power source may be provided via capacitive isolation. The capacitive isolation may be a pair of differential drivers providing a voltage signal from power source 120 through coupling capacitors C1-C4 to a rectifier formed by diodes D1-D4 electrically connected to and sourcing power for one or both of sensing circuitry 116 or stimulation generator 114, as shown in FIG. 5.

Figure 6:
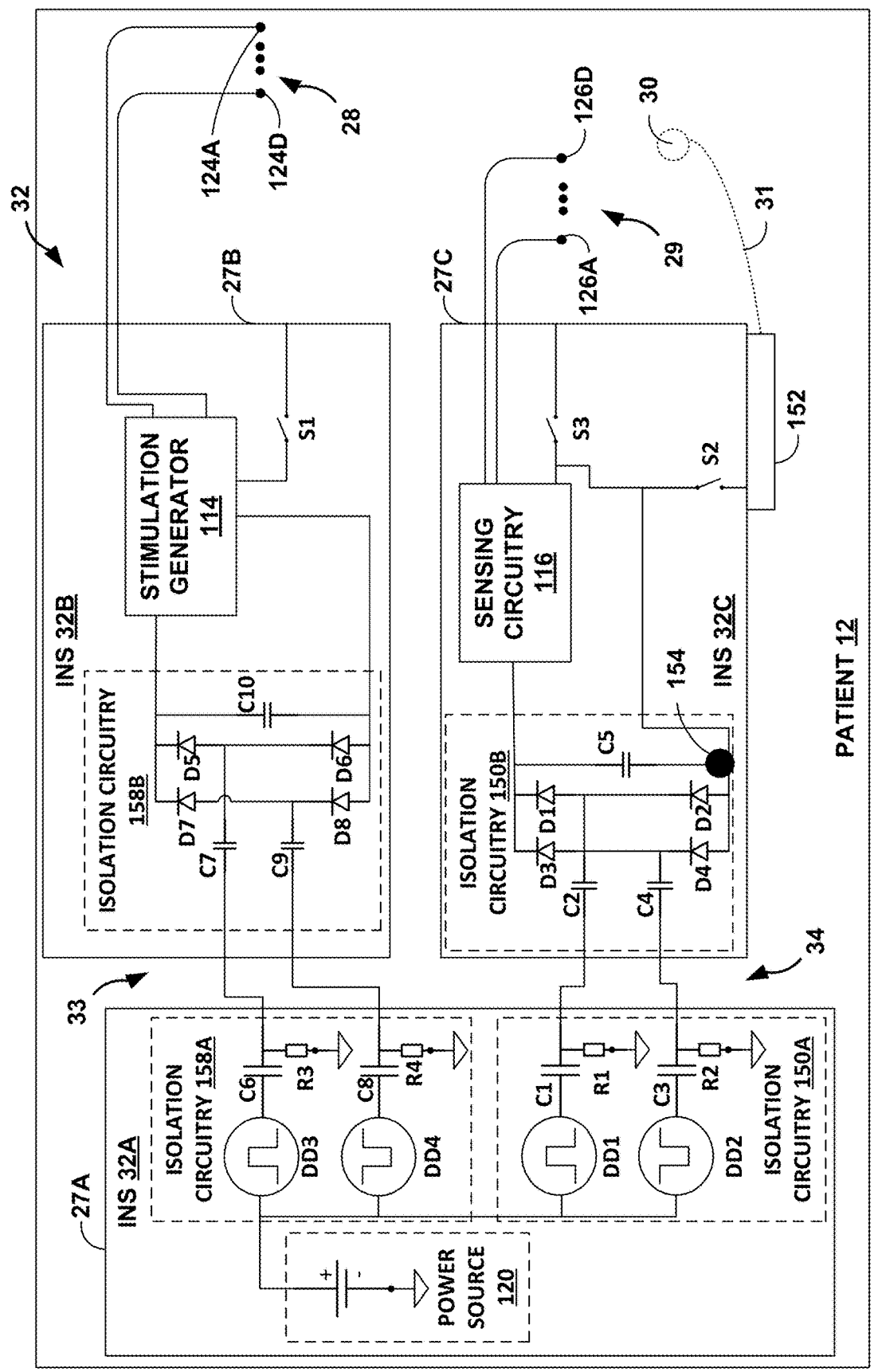
FIG. 6 is a functional block diagram illustrating an example INS of FIG. 2 that senses physiological signals while generating and delivering electrical stimulation to tissue of a patient.

In the example of FIG. 5, power source 120 provides power for a pair of differential voltage generators DD1 and DD2, both of which have programmable morphologies, amplitudes and frequencies. These differential voltage generators both drive a pair of series connected isolation capacitors C1 and C2, and C3 and C4. In some examples, only one capacitor without bias resistors may be needed for each of DD1 and DD2 as long as an appropriate level of AC isolation is maintained back to power source 120. However, a pair of series capacitors (e.g., C1 and C2, and C3 and C4) may be advantageous with the topology as shown in FIG. 6, where sensing circuitry 116 may not be in the same housing as the implantable neurostimulator. For example, full capacitive isolation in both sensing circuitry 116 and the implantable neurostimulator ensures that any fault conditions which may develop in any of electronics are fully isolated from the body tissue of patient 12.

In some examples, the center nodes of these isolation capacitors C1 and C2, and C3 and C4 may be weakly held at the most negative potential of the energy source via pulldown resistors R1 and R2. The center nodes of capacitors C1 and C2 and C3 and C4 may also be weakly tied together via a resistor. The rectified voltage from the rectifier is held on hold capacitor C5 which in turn is used to power sensing circuitry 116 with respect to the most negative voltage developed at the rectifier and reference node 154. In some examples, reference node 154 may be connected to an indifferent reference electrode 30 in the body tissue of patient 12. In some examples, the physiological signal may be sensed differentially.

In the example of FIG. 5, stimulation generator 114 may deliver electrical stimulation from at least two electrodes, such as electrodes 126A and 126C. As illustrated in FIG. 5, stimulation generator 114 is connected directly to power source 120, i.e., without being coupled via intervening isolation circuitry. However, in some examples, stimulation generator 114 may be connected to power source 120 via second isolation circuitry similar to isolation circuitry 150.

In some examples, DD1 and DD2 may have a drive frequency of approximately 10 kilohertz (kHz) to approximately 2 megahertz (MHz), such as approximately 200 (kHz) that provides a suitable balance between power transfer and efficiency. The capacitance of capacitors C1-C4 should be sufficiently small to provide enough AC impedance between sensing circuitry 116 and power source 120, but not so small as to disallow sufficient power transfer to sensing circuitry 116. In some examples, each capacitor of capacitors C1-C4 may have a capacitance of approximately 10 nanofarads (nF) to approximately 20 microfarad (µF), such as approximately 100 nF when sensing circuitry 116 is configured to detect target biomedical signals with spectral content from about 10 hertz (Hz to about 500 Hz. In some examples, the voltage of power source 120 may about 1 volt (V) to about 10 V, such as about 5 V.

The DC component of the impedance of the reference connection (e.g., the connection of reference node 154 to housing 27 and/or reference electrode 30) to sensing circuitry 116 may be decreased by the surface area size of the implantable reference electrode to allow sensing circuitry 116 to more closely "ride" on top of the common mode voltage introduced into the body tissue by the stimulation. The size of the reduction in the DC component is largely driven by the effective area of reference electrode 30. For example, a larger size of the implantable reference electrode may result in a larger reduction in the value of the DC component voltage received by reference node 154. With a reduced DC component of the impedance, a lower RMS noise may be achieved as a function of frequency along with the ability to better resolve small amplitude biomedical signals in the presence of large common mode aggressors. In other words, a reduced DC component of the impedance reduces the difference between the reference voltage and the potential of the body of patient 12, and reduces the magnitude of the common signal that must be rejected by sensing circuitry 116. Conversely, higher impedances result in higher common mode voltages appearing as a differential (real) signal, which is noise.

FIG. 6 is a functional block diagram of an example INS 32 of FIG. 2 that senses physiological signals while generating and delivering electrical stimulation to tissue of a patient. FIG. 6 is described with reference to FIGS. 2, 4, and 5. In the example of FIG. 6, INS 32 includes an implantable reference electrode (e.g., housing 27C and/or reference electrode 30 on lead 31), stimulation generator 114, sensing circuitry 116, power source 120, electrodes 124 and 126, connector block 152, and reference node 154 as described in FIGS. 4 and 5.

Additionally or alternatively, in the example of FIG. 6, INS 32 includes housings 27A-27C, conductors 33 and 34, and isolation circuitries 150A, 150B, 158A, and 158B. In some examples, housings 27A-27C, conductors 33 and 34 may correspond to housings 27A-27C and conductors 33 and 34 as described in FIG. 2. In some examples, isolation circuitries 150A and 150B (collectively "isolation circuitry 150") and isolation circuitries 158A and 158B (collectively "isolation circuitry 158") may correspond to isolation circuitry 150 as described in FIG. 5. For example, resistors R1 and R2, and R3 and R4 may be similar to resistors R1 and R2 as described in FIG. 5.

Although not illustrated in FIG. 6, any of housings 27A-27C may also comprise components similar to processor 110, memory 112, and telemetry circuitry 118 as described in FIG. 4. For example, housings 27A-27C may each include one or more processors, memory, and a telemetry circuitry similar to processor 110, memory 112, telemetry circuitry 118 as described in FIG. 4. In this example, housings 27B and 27C may also include a switching circuitry similar to switching circuitry 122 as described in FIG. 4. In this way, in some examples, housings 27A-27C may operate collectively as an implantable neurostimulator controller. In other examples, housing 27A may function as an implantable neurostimulator controller by controlling stimulation generator 114 and sensing circuitry 116 in housings 27B and 27C, respectively.

As illustrated in FIG. 6, INS 32 includes first housing 27A comprising power source 120, first portion of a first isolation circuitry 150A connected to power source 120, and a first portion of a second isolation circuitry 158A connected to power source 120. INS 32 further includes second housing 27C comprising a second portion of first isolation circuitry 150B connected to first portion of the first isolation circuitry 150A, sensing circuitry 116 connected to first isolation circuitry 150 and configured to detect a target biomedical signal of patient 12 via at least two implantable sensing electrodes 126A and 126D, and an implantable reference electrode connected to sensing circuitry 116.

Implantable reference electrode (e.g., housing 27C and/or reference electrode 30) is connected to sensing circuitry 116 and provides a common mode voltage introduced by electrical stimulation therapy to patient 12 to sensing circuitry 116. In some examples, reference electrode 30 may be connected to sensing circuitry 116 via lead 31, connector block 152, switch S2, and reference node 154. In other examples, implantable reference electrode may be housing 27C and connected to sensing circuitry 116 via switch S3 and reference node 154. In yet other examples, implantable reference electrode may be both reference electrode 30 and housing 27C and connected to sensing circuitry 116 via switches S2 and S3 and reference node 154. In some examples, switches S2 and S3 may not be used, but instead there may be a direct connection between sensing circuitry 116 and reference node 154. In some examples, sensing circuitry 116 does not share a ground with power source 120 and stimulation generator 114 because of isolation circuitry 150. In some examples, switches S2 and S3 may be controlled by processor 110 as described in FIG. 4.

INS 32 further includes third housing 27B comprising second portion of the second isolation circuitry 158B connected to first portion of the second isolation circuitry 158A, and stimulation generator 114 connected to second isolation circuitry 158 and configured to deliver electrical stimulation therapy to patient 12 via at least two stimulation electrodes 124A and 124D. In some examples, stimulation generator 114 may use housing 27B as a stimulation electrode or return electrode via switch S1. In these examples, switch S1 may be controlled by processor 110 as described in FIG. 4. In some examples, housing 27B may be connected to a potential defined by stimulation generator 114, which may be the lowest potential of the rectifier formed by diodes D5-D8 as well. In some examples, switch S1 may not be used, but instead there may be a direct connection between stimulation generator 114 and housing 27B.

In the example of FIG. 6, first isolation circuitry 150 (including portions 150A and 150B) is configured to isolate a voltage received from power source 120 and supply the isolated voltage to sensing circuitry 116, and second isolation circuitry 158 (including portions 158A and 158B) is configured to isolate a voltage received from power source 120 and supply the isolated voltage to stimulation generator 114. In other words, first isolation circuitry 150 and second isolation circuitry 158 are each separate floating power supplies. In this example, sensing circuitry 116 does not share a ground with power source 120 and stimulation generator 114.

In some examples, first isolation circuitry 150 may be configured to provide AC coupling between power source 120 and sensing circuitry 116. In some examples, first portion of the first isolation circuitry 150A comprises first differential voltage generator DD1 configured to drive one or more first coupling capacitors C1, and second differential voltage generator DD2 configured to drive one or more second coupling capacitors C3. In some examples, INS 32 may connect to an extension cable which provides the differential power signals from first and second differential voltage generators DD1 and DD2 to the separate housings 27B and 27C (of which there may be multiples of each). In other words, although FIG. 6 illustrates three separate housings 27A-27C, it is possible to have any number of separate housings, where housing 27A has a common power source (e.g., power source 120).

In some examples, second portion of the first isolation circuitry 150B comprises a rectifier formed by diodes D1-D4 configured to rectify a voltage from the one or more first and second coupling capacitors C2 and C4, and hold capacitor C5 configured to receive the rectified voltage from the rectifier.

In some examples, first differential voltage generator DD1 is configured to produce a fifty percent duty cycle square wave with a five volt amplitude, and second differential voltage generator DD2 is configured to produce a fifty percent duty cycle square wave with the opposite polarity of first differential voltage generator DD1. The square wave produced by each of the first and second differential voltage generators DD1 and DD2 may have a frequency of approximately to two hundred kilohertz (kHz). In some examples, the rectifier may be at least one of a full-wave rectifier, a synchronous rectifier, or a half-wave rectifier. In some examples, the rectifier may comprise a reference node connected to the at least one implantable reference electrode.

In some examples, implantable reference electrode 30 may be configured to provide the common mode voltage introduced by electrical stimulation therapy to patient 12 to sensing circuitry 116 comprises hold capacitor C5 that is configured to power sensing circuitry 116 with respect to a voltage at reference node 154 provided by implantable reference electrode 30. In some examples, first and second one or more coupling capacitors C1-C4 each may have a capacitance substantially close one hundred nanofarads (nF). In some examples, first portion of the first isolation circuitry 150A may comprise a DC-to-AC transformer, and second portion of the first isolation circuitry 150B may comprise a rectifier configured to rectify a voltage from the DC-to-AC transformer and a hold capacitor configured to receive the rectified voltage from the rectifier.

In some examples, first portion of the second isolation circuitry 158A may comprise a third differential voltage generator DD3 configured to drive one or more third coupling capacitors C6, and fourth differential voltage generator DD4 configured to drive one or more fourth coupling capacitors C8. In some examples, second portion of the second isolation circuitry 158B may comprise a rectifier formed by diodes D5-D8 configured to rectify a voltage from the one or more third and fourth coupling capacitors C7 and C9, and hold capacitor C10 configured to receive the rectified voltage from the rectifier. In some examples, third differential voltage generator DD3 may be configured to produce an approximately fifty percent duty cycle square wave with an approximately five volt amplitude, and fourth differential voltage generator DD4 may be configured to produce the opposite polarity of third differential voltage generator DD3. The square wave produced by each of the third and fourth differential voltage generators DD3 and DD4 may have a frequency of approximately two hundred kilohertz (kHz).

In some examples, sensing circuitry 116 may be configured to sense physiological signals with spectral content having a frequency between approximately one hertz (Hz) and approximately five hundred Hz or greater. In some examples, implantable reference electrode 30 comprises a connection to housing 27C or implantable electrode via lead 31.

Figure 7:
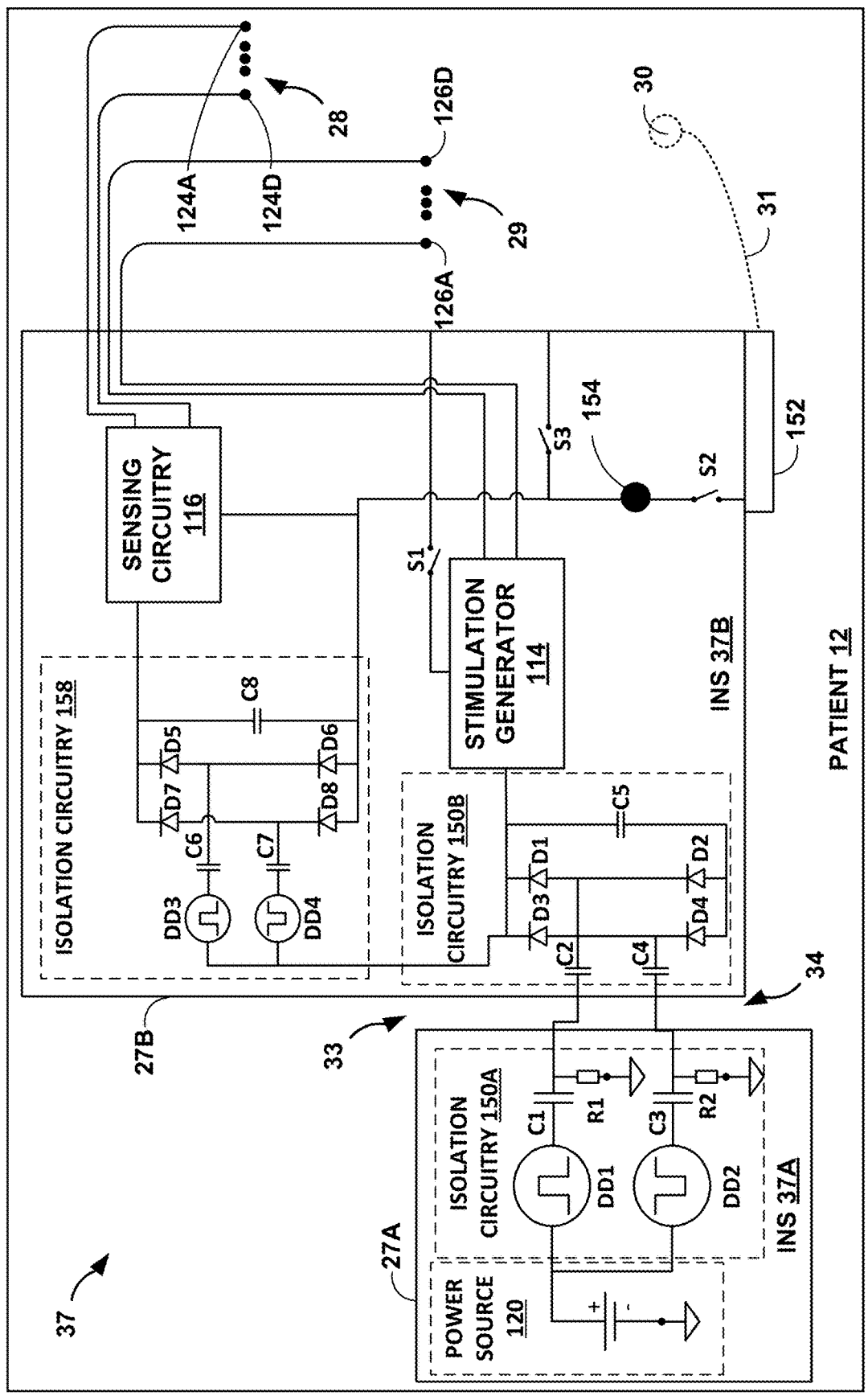
FIG. 7 is a functional block diagram illustrating an example INS of FIG. 3 that senses physiological signals while generating and delivering electrical stimulation to tissue of a patient.

FIG. 7 is a functional block diagram of an example distributed INS 37 of FIG. 3 that senses physiological signals while generating and delivering electrical stimulation to tissue of a patient. FIG. 7 is described with reference to FIGS. 3-6. For example, INS 37 includes an implantable reference electrode, stimulation generator 114, sensing circuitry 116, power source 120, electrodes 124 and 126, connector block 152, and reference node 154 as described in FIGS. 4 and 5. Additionally or alternatively, in the example of FIG. 7, INS 37 includes housings 27A and 27B, conductors 33 and 34, and isolation circuitries 150A, 150B, and 158. In some examples, housings 27A and 27B and conductors 33 and 34 may correspond to housings 27A and 27B and conductors 33 and 34 as described in FIG. 3. In some examples, isolation circuitries 150A and 150B (collectively "isolation circuitry 150") and isolation circuitry 158 may correspond to isolation circuitries 150 and 158 as described in FIG. 6.

As illustrated in FIG. 7, INS 37 comprises housing 27A, housing 27B, and conductors 33 and 34. Although not illustrated in FIG. 7, at least one of housings 27A and 27B may comprise components similar to processor 110, memory 112, and telemetry circuitry 118 as described in FIG. 4. For example, one or both of housings 27A and 27B may include one or more processors, memory, and a telemetry circuitry similar to processor 110, memory 112, telemetry circuitry 118 as described in FIG. 4. In this example, housing 27B may also include a switching circuitry similar to switching circuitry 122 as described in FIG. 4. In this way, in some examples, housings 27A and 27B may operate collectively as an implantable neurostimulator controller. In other examples, housing 27A may function as an implantable neurostimulator controller by controlling stimulation generator 114 and sensing circuitry 116 in housing 27B.

Housing 27A comprises power source 120 and first portion of first isolation circuitry 150A connected to power source 120. Housing 27B comprises second portion of the first isolation circuitry 150B connected to first portion of the first isolation circuitry 150A to form first isolation circuitry 150, second isolation circuitry 158 connected to second portion of the first isolation circuitry 150B, and sensing circuitry 116 connected to second isolation circuitry 158 and configured to detect a target biomedical signal of patient 12 via at least two implantable sensing electrodes 124A and 124D.

Implantable reference electrode (e.g., housing 27B and/or reference electrode 30) is connected to sensing circuitry 116 and provides a common mode voltage introduced by electrical stimulation therapy to patient 12 to sensing circuitry 116. In some examples, the implantable reference electrode may be reference electrode 30 that is connected to sensing circuitry 116 via lead 31, connector block 152, switch S2, and reference node 154. In other examples, the implantable reference electrode may be housing 27C that is connected to sensing circuitry 116 via switch S3 and reference node 154. In yet other examples, the implantable reference electrode may be both reference electrode 30 and housing 27B and connected to sensing circuitry 116 via switches S2 and S3 and reference node 154. In some examples, switches S2 and S3 may be controlled by processor 110 as described in FIG. 4.

Housing 27B further comprises stimulation generator 114 connected to second portion of the first isolation circuitry 150B and configured to deliver electrical stimulation therapy to patient 12 via at least two stimulation electrodes 126A and 126D. In some examples, stimulation generator 114 may use housing 27B as a stimulation electrode or return electrode via switch S1. In these examples, switch S1 may be controlled by processor 110 as described in FIG. 4. In some examples, housing 27B may be connected to a potential defined by stimulation generator 114, which may be the lowest potential of the rectifier formed by diodes D1-D4 as well. In some examples, switch S1 may not be used, but instead there may be a direct connection between stimulation generator 114 and housing 27B.

First isolation circuitry 150, including first portion 150A and second portion 150B, is configured to isolate a first voltage received from power source 120 and provide the isolated first voltage to stimulation generator 114 and second isolation circuitry 158. Second isolation circuitry 158 is configured to isolate a second voltage received from first isolation circuitry 150 and provide the isolated second voltage to sensing circuitry 116. In this way, sensing circuitry 116 does not share a ground with power source 120 and stimulation generator 114.

In some examples, first isolation circuitry 150 may be configured to provide AC coupling between power source 120 and stimulation generator 114 and provide AC coupling between power source 120 and second isolation circuitry 158. In some examples, first portion of the first isolation circuitry 150 may comprise first differential voltage generator DD1 configured to drive one or more first coupling capacitors C1, and second differential voltage generator DD2 configured to drive one or more second coupling capacitors C3. In some examples, second portion of the first isolation circuitry 150B may comprise a rectifier formed by diodes D1-D4 configured to rectify a voltage from the one or more first and second coupling capacitors C2 and C4, and hold capacitor C5 configured to receive the rectified voltage from the rectifier.

In some examples, first differential voltage generator DD1 may be configured to produce a fifty percent duty cycle square wave with a five volt amplitude, and wherein the second differential voltage generator is configured to produce a fifty percent duty cycle square wave with the opposite polarity of the first differential voltage generator. In these examples, the square wave be produced by each of the first and second differential voltage generators DD1 and DD2 may have a frequency of approximately two hundred kilohertz (kHz).

In some examples, the rectifier (e.g., formed by diodes D1-D4 or D5-D8) may be at least one of a full-wave rectifier, a synchronous rectifier, or a half-wave rectifier. In some examples, the rectifier may comprise a reference node connected to the implantable reference electrode (e.g., housing 27 or electrode 30). In some examples, the implantable reference electrode may be configured to provide the common mode voltage introduced by electrical stimulation therapy to patient 12 to sensing circuitry 116 comprises wherein hold capacitor C5 may be configured to power sensing circuitry 116 with respect to a voltage at reference node 154 provided by the implantable reference electrode.

In some examples, first and second one or more coupling capacitors C1-C4 each may have a capacitance substantially close to one hundred nanofarads (nF). In some examples, first portion of the first isolation circuitry 150A may comprise a DC-to-AC transformer. In some examples, second portion of the first isolation circuitry 150B may comprise a rectifier formed by diodes D1-D4 configured to rectify a voltage from the DC-to-AC transformer and hold capacitor C5 that is configured to receive the rectified voltage from the rectifier.

In some examples, second isolation circuitry 158 may comprise third differential voltage generator DD3 configured to drive one or more third coupling capacitors C6, fourth differential voltage generator DD4 configured to drive one or more fourth coupling capacitors, a rectifier configured to rectify a voltage from the one or more third and fourth coupling capacitors; and hold capacitor C10 configured to receive the rectified voltage from the rectifier. In these examples, third differential voltage generator DD3 may be configured to produce a fifty percent duty cycle square wave with a five volt amplitude, and fourth differential voltage generator DD4 may be configured to produce the opposite polarity of third differential voltage generator DD3.

In some examples, sensing circuitry 116 may be configured to sense physiological signals with spectral content having a frequency between one hertz (Hz) and five hundred Hz or greater. In some examples, the implantable reference electrode may comprise a connection to at least one of housing 27B or implantable electrode 30.

In the example of FIG. 7, nested rectification is employed within housing 27B where both stimulation generator 114 and sensing circuitry 116 are AC powered from power source 120 in housing 27A. Nested rectification may be a second stage of isolation and may provide further AC isolation than a single stage of isolation. In the example of FIG. 7, sensing circuitry 116 is connected to the nested rectifier of second isolation circuitry 158 in housing 27B, and stimulation generator 114 is connected to the main rectifier of first isolation circuitry 150. Alternatively, in some examples, sensing circuitry 116 may be connected to the main rectifier of first isolation circuitry 150 in housing 27B, and stimulation generator 114 may be connected to the nested rectifier of second isolation circuitry 158. In some examples, housing 27B may be used as a stimulation electrode for stimulation generator 114.

Figure 8:
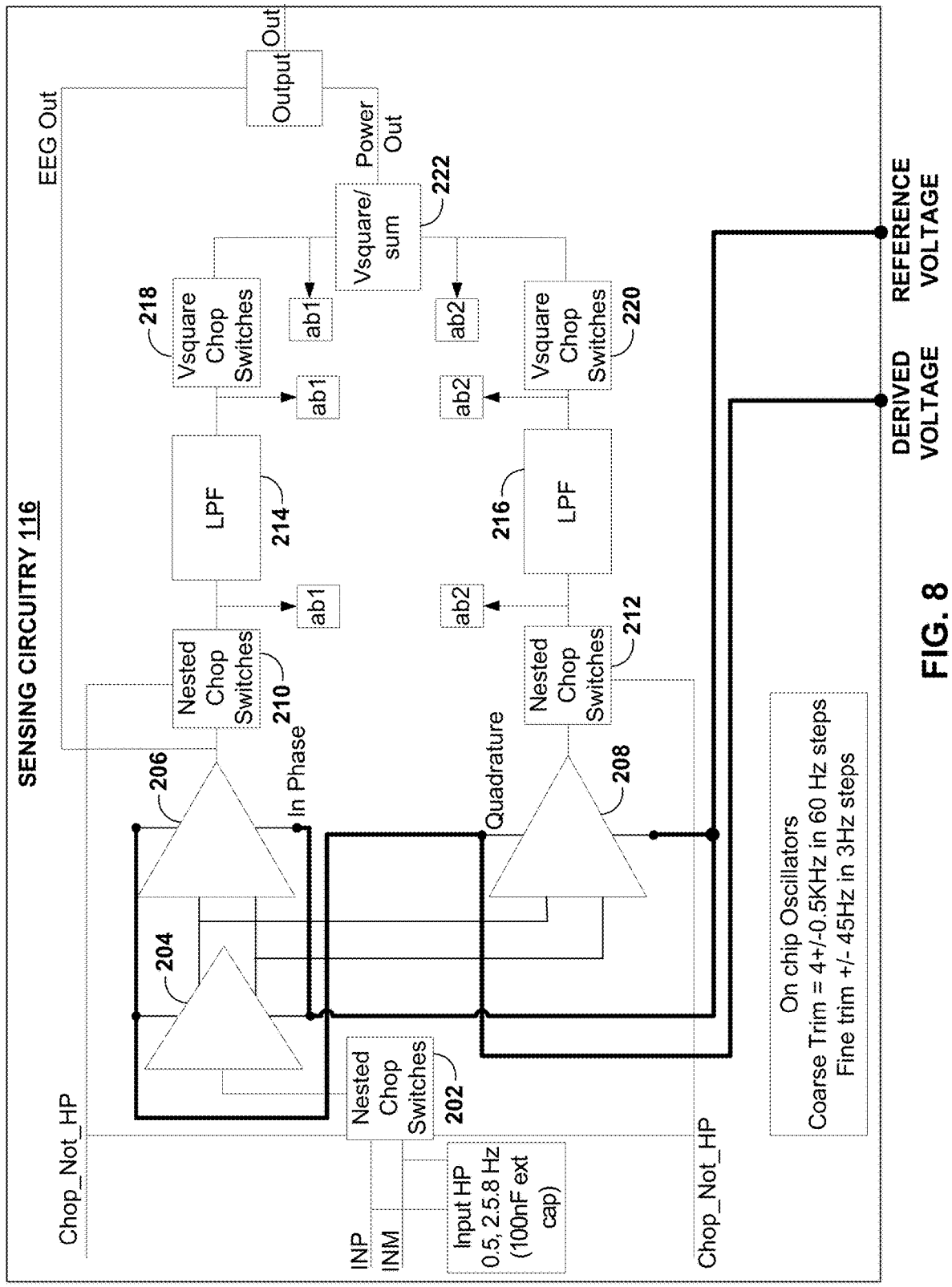
FIG. 8 is a functional block diagram illustrating an example of sensing circuitry that may be used with an INS as shown in FIGS. 1-7.

FIG. 8 is a functional block diagram illustrating example sensing circuitry 116 that may be used with an INS as shown in FIGS. 1-7. In the example of FIG. 8, sensing circuitry 116 includes amplifiers 204-208 (e.g., forming an instrumentation amplifier), nested chop switches 202, 210, and 212, low pass filters 214 and 216, Vsquare chop switches 218 and 220, and Vsquare/sum 222. Additional information regarding, for example, sensing circuitry and/or instrumentation amplifiers may be found in U.S. Patent Publication No. 2009/0082691 A1, filed Sep. 25, 2008, entitled "FREQUENCY SELECTIVE MONITORING OF PHYSIOLOGICAL SIGNALS," the entire contents of which being incorporated herein by reference.

Nested chop switches 202 may receive the inputs of sensing circuitry 116 and may have a chopper frequency of 64 hertz (Hz) (i.e., Fchop of switches 202 may be equal to approximately 64 Hz). Amplifiers 204 may receive the output from nested chop switches 202 and may have a gain of 10 or may be bypassed (e.g., Av of amplifiers 204 may be equal to approximately 10 or amplifiers 204 may be bypassed). Amplifiers 206 and 208 each may receive the output from amplifier 204 and may have a gain of 500, 1000, or 2000 (e.g., Av of amplifiers 206 and 208 may be equal to approximately 500, 1000, or 2000). Nested chop switches 210 and 212 may each receive the output from amplifiers 206 and 208, respectively, and may have a chopper frequency of approximately 64 Hz (i.e., Fchop of switches 210 and 212 may be equal to approximately 64 Hz). Low pass filters 214 and 216 may receive the output from nested chop switches 210 and 212, respectively, and each may be an approximately 5-16 Hz 3 pole and an approximately 10-32 Hz 2 pole low pass filter. Vsquare chop switches 218 and 220 may receive the output from low pass filter 214 and 216, respectively, and each may have a chopper frequency of approximately 128 Hz (i.e., Fchop of switches 218 and 220 may be equal to approximately 128 Hz). Vsquare/sum 222 may receive the outputs from both Vsquare chop switches 218 and 220 and my output a sensed signal.

The most negative potential for all the circuit elements shown in FIG. 8, typically referred to as VSS, GND, VEE or any other term in the art, is tied to reference node 154 as described in FIGS. 5-7. As illustrated in FIG. 8, the lower power rails of amplifiers 202-206 received the reference voltage from reference node 154. In some examples, amplifiers 202-206 may be differential amplifiers that reference the differential inputs using the reference voltage.

As illustrated in FIG. 8, the high power rails of amplifiers 202-206 received a derived voltage from the voltage at hold capacitor C5. For example, the derived voltage may be from an optional low drop out (LDO) regulator in series with hold capacitor C5. In this way, the most negative potential of the rectifier and of sensing circuitry 116 is at reference node 154 that is connected to the body tissue through a low ohmic connection to an implantable reference electrode. When a common mode voltage is received at the implantable reference electrode, the common mode voltage will be part of the reference voltage applied to both the rectifier and sensing circuitry 116. The reference voltage is lowest potential at both the rectifier and sensing circuitry 116. As illustrated in FIG. 8, in some examples, the amplifiers of sensing circuitry 116 use for reference the reference voltage.

Figure 9:
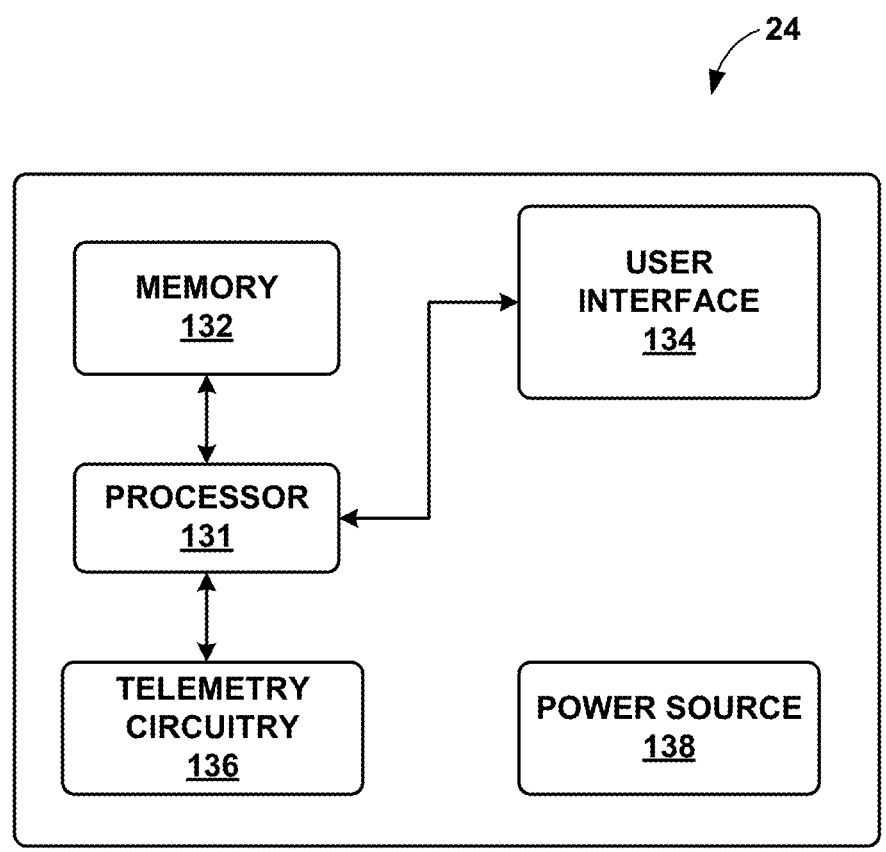
FIG. 9 is a functional block diagram illustrating an example medical device programmer.

FIG. 9 is a functional block diagram illustrating an example medical device programmer 24. As shown in FIG. 9, programmer 24 includes processor 131, memory 132, user interface 134, telemetry circuitry 136, and power source 138. Programmer 24 may be a dedicated hardware device with dedicated software for programming INS 26. Alternatively, programmer 24 may be an off-the-shelf computing device running an application that enables programmer 24 to program INS 26. In some examples, separate programmers may be used to program INS 26.

A user may use programmer 24 to select therapy programs (e.g., sets of stimulation parameters), generate new therapy programs, modify therapy programs through individual or global adjustments or transmit the new programs to a medical device, such as INS 26 (FIG. 1). The clinician may interact with programmer 24 via user interface 134, which may include display to present graphical user interface to a user, and a keypad or another mechanism for receiving input from a user.

Processor 131 can take the form one or more microprocessors, DSPs, ASICs, FPGAs, programmable logic circuitry, or the like, and the functions attributed to processor 131 herein may be embodied as hardware, firmware, software or any combination thereof. Memory 132 may store instructions that cause processor 131 to provide the functionality ascribed to programmer 24 herein, and information used by processor 131 to provide the functionality ascribed to programmer 24 herein.

Memory 132 may include any fixed or removable magnetic, optical, or electrical media, such as RAM, ROM, CD-ROM, a hard magnetic disk, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery INS 26, such as stimulation parameter values.

Programmer 24 may communicate wirelessly with INS 26, such as using RF communication or proximal inductive interaction. This wireless communication is possible through the use of telemetry circuitry 136, which may be coupled to an internal antenna or an external antenna. Telemetry circuitry 136 may be similar to telemetry circuitry 118 of INS 26 as described in FIG. 4.

Telemetry circuitry 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

Figure 10:
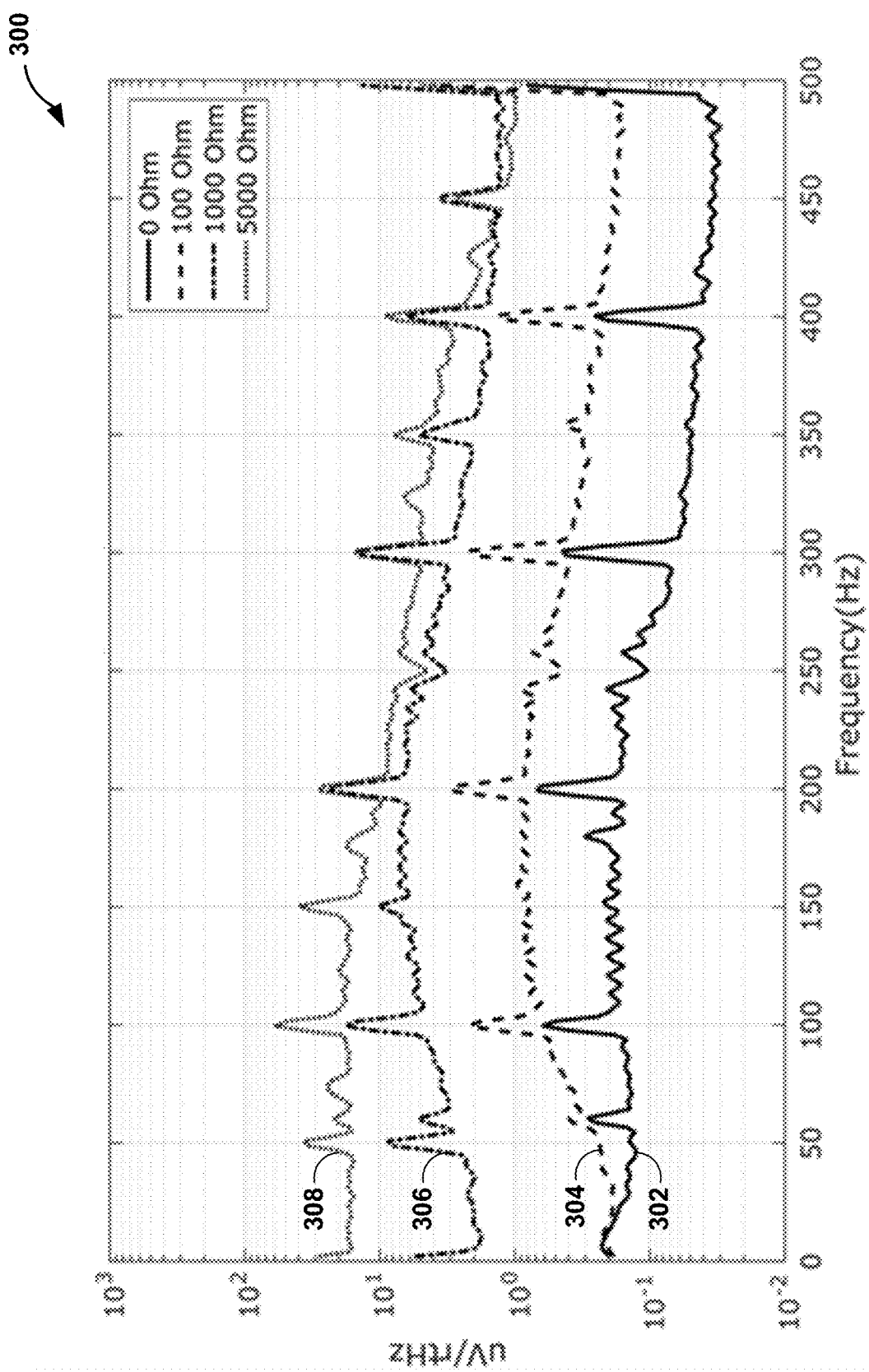
FIG. 10 is a graph illustrating the root mean square (RMS) noise versus frequency as detected by the sensing circuitry of FIG. 8 with various DC impedances.

FIG. 10 is a graph illustrating the root mean square (RMS) noise versus frequency as detected by the sensing circuitry of FIG. 8 with various DC impedances. As illustrated in FIG. 10, graph 300 includes impedance traces 302-308, each corresponding to one of a plurality of different DC impedances between reference electrode 30 and the reference node as described in FIGS. 5-7. In the example of FIG. 10, the stimulation signal parameters for a stimulation source are a frequency of approximately 100 Hz, a current amplitude of approximately 3 mA, and a duration of approximately 50 µs applied into a body phantom filled with approximately 0.9% saline. In the example of FIG. 10, reference electrode 30 is composed of an approximately 3 $cm^2$ titanium slug, and the bipolar sensing electrodes are approximately 5 $mm^2$ polished platinum rings.

Impedance trace 302 represents the RMS noise versus frequency as detected by the sensing circuitry with zero DC impedance. Impedance trace 304 represents the RMS noise versus frequency as detected by the sensing circuitry with approximately 100 ohms ($\Omega$) of DC impedance. Impedance trace 306 represents the RMS noise versus frequency as detected by the sensing circuitry with approximately 1000 ohms ($\Omega$) of DC impedance. Impedance trace 308 represents the RMS noise versus frequency as detected by the sensing circuitry with approximately 5000 ohms ($\Omega$) of DC impedance.

As illustrated in FIG. 4, the DC component of the impedance of the reference connection (e.g., the connection between reference electrode 30 and the reference node) to the sensing circuitry may be reduced to lower the RMS noise floor. Reducing the DC component of the impedance allows the sensing circuitry to more closely "ride" on top of the common mode voltage introduced into the body tissue by the stimulation and observed by the inputs of sensing circuitry 116. Additionally, the DC component is largely driven by the effective area of reference electrode 30. In this way, increasing the effective area of reference electrode 30 may lower RMS noise as a function of frequency along with the ability to better resolve small amplitude target biomedical signals in the presence of large common mode voltages in sensed physiological signals.

Figure 11:
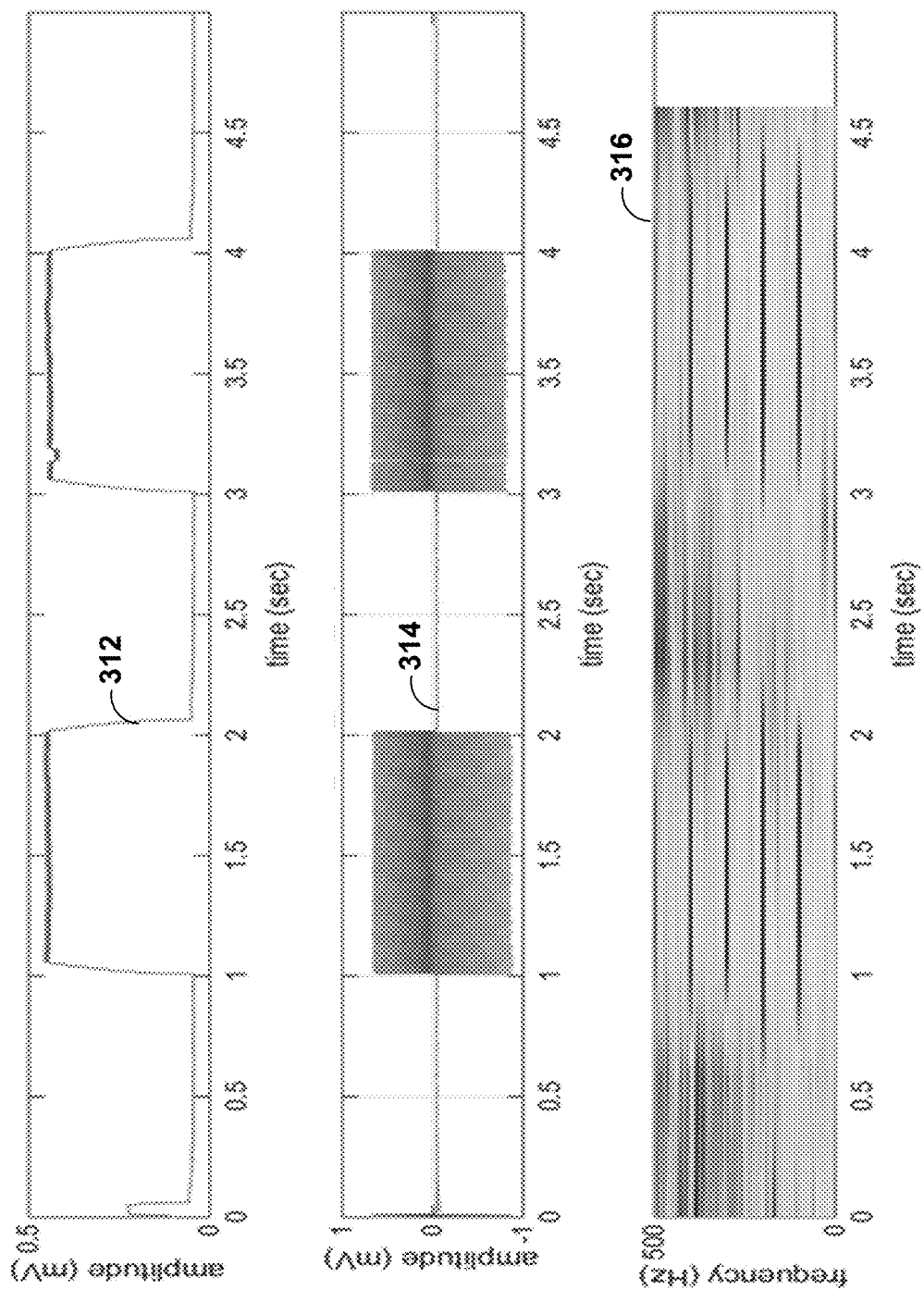
FIG. 11 is a graph illustrating a time domain output of conventional sensing circuitry when sensing during repeated stimulation bursts.

FIG. 11 is a graph illustrating a time domain output of conventional sensing circuitry when sensing during repeated stimulation bursts. In the example of FIG. 11, graph 310 includes RMS noise 312, physiological signal 314, and frequency of physiological signal 316.

In the example of FIG. 11, a stimulator connected to a battery is configured to generate a one second block of approximately 100 Hz, 2 mA, 100 μs pulse width stimulation once every two seconds. The sensing circuitry is configured to sense differentially in the same saline-filled body phantom where the stimulator is delivering energy. As illustrated by FIG. 11, the sensing circuitry is saturated by the 1.2 mV peak-to-peak stimulation aggressor in physiological signal 314. The stimulation aggressor also causes corresponding peaks in the frequency of physiological signal 316. As illustrated by FIG. 11, RMS noise 312 of the stimulation aggressor during stimulation is almost 400 μV, which is several orders of magnitude larger than the low amplitude target biomedical signals.

Figure 12:
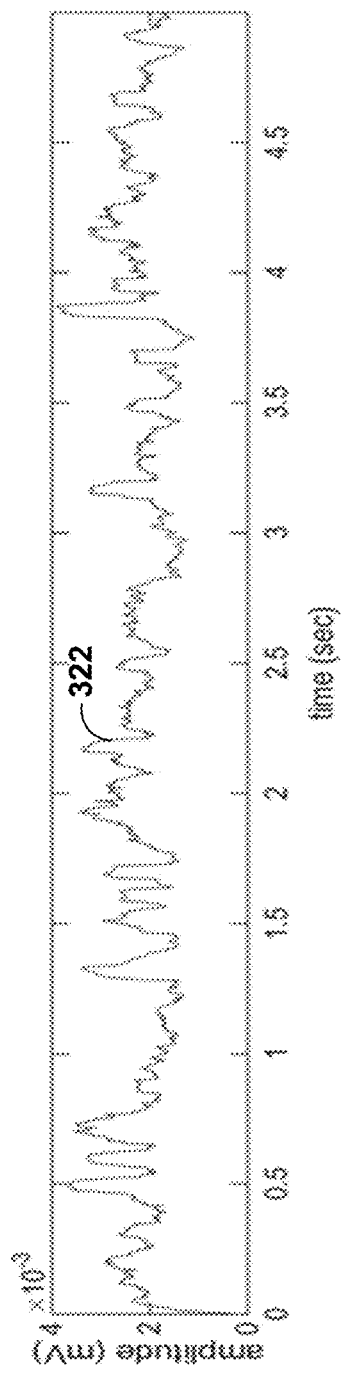
FIG. 12 is a graph illustrating a time domain output of sensing circuitry when sensing during repeated stimulation bursts, in accordance with the techniques described herein.

FIG. 12 is a graph illustrating a time domain output of sensing circuitry when sensing during repeated stimulation bursts, in accordance with techniques described herein. FIG. 12 is described with reference to FIG. 4. In the example of FIG. 12, graph 320 includes RMS noise 322, physiological signal 324, and frequency of physiological signal 326.

In the example of FIG. 12, stimulation generator 114 connected to power source 120 is configured to generate a one second block of approximately 100 Hz, 2 mA, 100 μs pulse width stimulation once every two seconds. The sensing circuitry is configured to sense differentially in the same saline-filled body phantom where the stimulator is delivering energy. As illustrated by FIG. 12, the sensing circuitry is not saturated by the 1.2 mV peak-to-peak stimulation aggressor in physiological signal 314, but instead the effects of the stimulation aggressor do not occur. The stimulation aggressor also no longer causes any peaks in the frequency of physiological signal 316. As illustrated by FIG. 12, RMS noise 312 of the stimulation aggressor during stimulation may have an amplitude of approximately 2 to 4 microvolts (μV), which is not several orders of magnitude greater than the low amplitude target biomedical signals, but instead substantially closer to the amplitude for target biomedical signals of about 1 μV to about 100 μV.

Figure 13:
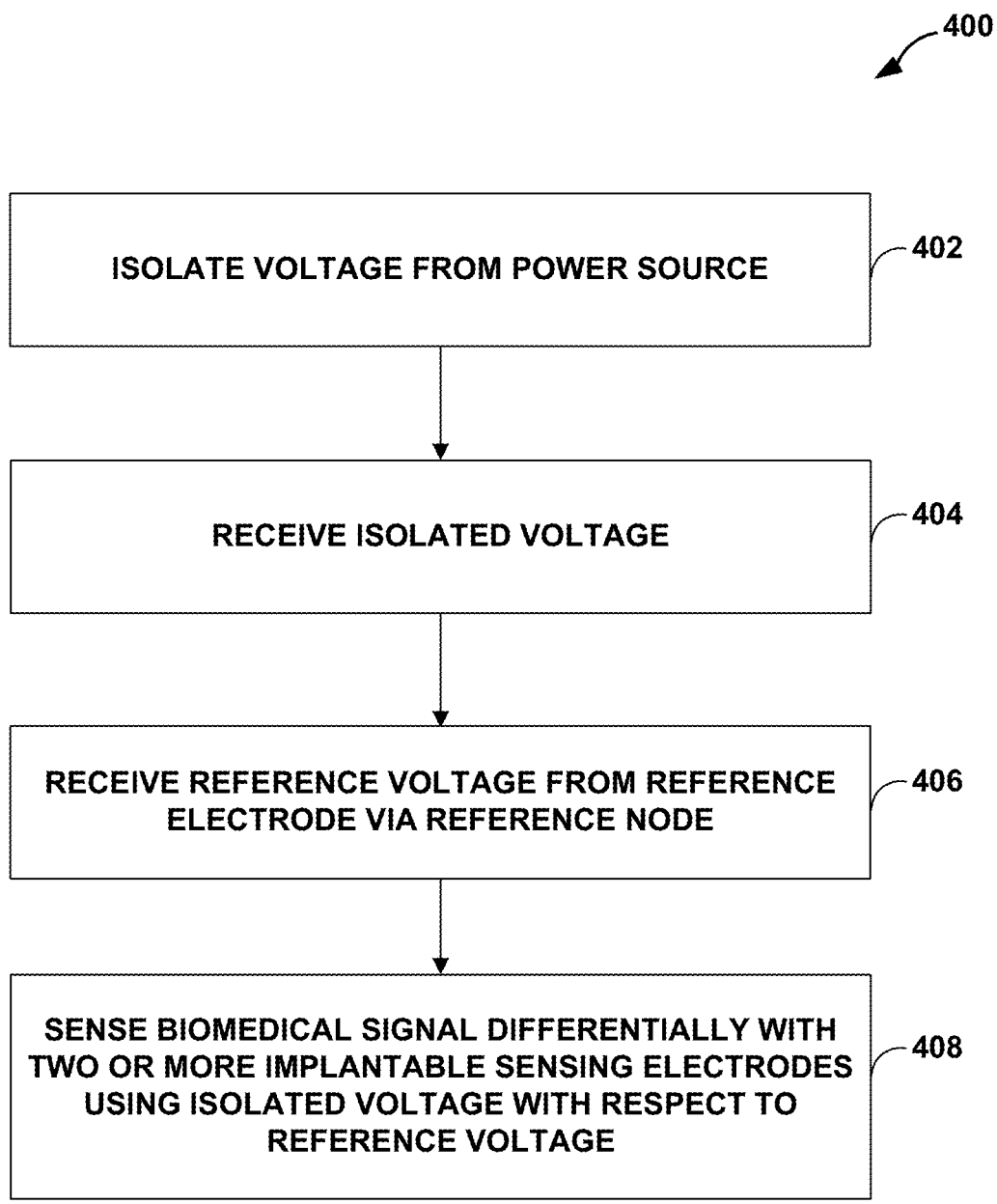
FIG. 13 is a flowchart illustrating an example technique for sensing a biomedical signal of a patient.

FIG. 13 is a flowchart illustrating example technique 400 for sensing a biomedical signal of a patient. For ease of understanding, technique 400 of FIG. 13 is described with reference to the operation of the sensing circuitry of FIG. 5. However, technique 400 may also be applicable to FIGS. 6 and 7.

In the example of FIG. 13, isolation circuitry 150 isolates a voltage from power source 120 (402). In some examples, isolating the voltage from the power source comprises driving, by first differential voltage generator DD1, one or more first coupling capacitors C1 and C2, driving, by second differential voltage generator DD2, one or more second coupling capacitors C3 and C4, rectifying, by a rectifier formed by diodes D1-D4, a voltage from the one or more first and second coupling capacitors C1-C4, and receiving, by hold capacitor C5, the rectified voltage from the rectifier. In some examples, first differential voltage generator DD1 may be configured to produce a fifty percent duty cycle square wave with a five volt amplitude, and second differential voltage generator DD2 may be configured to produce a fifty percent duty cycle square wave with the opposite polarity of first differential voltage generator DD1.

In some examples, the square wave produced by each of the first and second differential voltage generators DD1 and DD2 may have a frequency substantially close to two hundred kilohertz (kHz). In some examples, the rectifier may be at least one of a full-wave rectifier, a synchronous rectifier, or a half-wave rectifier. In some examples, the rectifier comprises a reference node connected to the implantable reference electrode. In some examples, first and second one or more coupling capacitors C1-C4 each may have a capacitance substantially close to one hundred nanofarads (nF).

In some examples, isolating the voltage from the power source comprises generating, by a power inverter comprising a transformer, an AC voltage from a DC voltage, rectifying, by a rectifier formed by diodes D1-D4, a second DC voltage from the AC voltage, and receiving, by hold capacitor C5, the second DC voltage from the rectifier.

In the example of FIG. 13, sensing circuitry 116 receives the isolated voltage from isolation circuitry 150 (404). In the example of FIG. 13, sensing circuitry 116 receives a reference voltage from a reference electrode via a reference node (406). In the example of FIG. 13, sensing circuitry 116 detects a target biomedical signal differentially with two or more implantable sensing electrodes using the isolated voltage with respect to the reference voltage (408). In some examples, wherein the target biomedical signal comprises spectral content having a frequency between one hertz (Hz) and five hundred Hz or greater. In some examples, the reference voltage from the reference electrode comprises a common mode potential from electrostimulation of tissue of a patient.

In addition, any of the described units, devices, or components may be implemented together or separately as discrete but interoperable devices. Depiction of different features as units or components is intended to highlight different functional aspects and does not necessarily imply that such units or components must be realized by separate hardware or software components. Rather, functionality associated with one or more units or components may be performed by separate hardware or software components, or integrated within common or separate hardware or software components.

When implemented in software, the functionality ascribed to the techniques, devices, and systems described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure. In some examples, computer-readable storage media may comprise non-transitory media. The term "non-transitory" may indicate that the storage medium is tangible and is not embodied in a carrier wave or a propagated signal. In certain examples, a non-transitory storage medium may store data that can, over time, change (e.g., in RAM or cache).

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

Various examples have been described. These and other examples are within the scope of the following claims.

The invention claimed is:

1. A method comprising:
    isolating, by isolation circuitry connected to a power source, a voltage from the power source;
    receiving, by sensing circuitry, the isolated voltage from the isolation circuitry;
    receiving, by the sensing circuitry and via a reference node connected to a low power rail in the sensing circuitry, a reference voltage from an implantable reference electrode connected to the reference node; and
    sensing, by the sensing circuitry and via at least two or more implantable sensing electrodes, a biomedical signal of a patient using the isolated voltage with respect to the reference voltage.

2. The method of claim 1, wherein the reference voltage from the implantable reference electrode comprises a common mode potential introduced by electrical stimulation therapy delivered to the patient.

3. The method of claim 1, wherein isolating the voltage from the power source comprises:
    driving, by a first differential voltage generator, one or more first coupling capacitors;
    driving, by a second differential voltage generator, one or more second coupling capacitors;
    rectifying, by a rectifier, a voltage from the one or more first and second coupling capacitors; and
    receiving, by a hold capacitor, the rectified voltage from the rectifier.

4. The method of claim 3, wherein the first differential voltage generator is configured to produce a square wave, and wherein the second differential voltage generator is configured to produce a square wave with a polarity opposite to a polarity of the square wave of the first differential voltage generator.

5. The method of claim 4, wherein the square wave produced by each of the first and second differential voltage generators has a frequency of approximately two hundred kilohertz (kHz).

6. The method of claim 3, wherein the rectifier is at least one of a full-wave rectifier, a synchronous rectifier, or a half-wave rectifier.

7. The method of claim 1, wherein isolating the voltage from the power source comprises:
    generating, by a power inverter comprising a transformer, an AC voltage from a DC voltage;
    rectifying, by a rectifier, a second DC voltage from the AC voltage; and
    receiving, by a hold capacitor, the second DC voltage from the rectifier.

8. The method of claim 1, wherein the biomedical signal comprises spectral content having a frequency between approximately one hertz (Hz) and approximately five hundred Hz.

9. The method of claim 1, further comprising:
    delivering, by stimulation circuitry and via at least two implantable stimulation electrodes, electrical stimulation therapy to the patient.

10. A system comprising:
    means for isolating a voltage from the power source;
    means for receiving the isolated voltage from the isolation circuitry;
    means for receiving, via a reference node connected to a low power rail, a reference voltage from an implantable reference electrode that is connected to the reference node; and
    means for sensing a biomedical signal of a patient with two or more implantable sensing electrodes using the isolated voltage with respect to the reference voltage.

11. The system of claim 10, further comprising:
    means for delivering electrical stimulation therapy to the patient, wherein the reference voltage from the implantable reference electrode comprises a common mode potential introduced by the electrical stimulation therapy.

12. The system of claim 10, wherein the means for isolating the voltage comprise:
    means for driving one or more first coupling capacitors;
    means for driving one or more second coupling capacitors;
    means for rectifying a voltage from the one or more first and second coupling capacitors; and
    means for receiving the rectified voltage from the rectifier.

13. The system of claim 12, wherein the means for driving the one or more first coupling capacitors comprises means for producing a square wave with a first polarity, and wherein the means for driving the one or more second coupling capacitors comprises means for producing a square wave with a second polarity that opposite to the first polarity.

14. The system of claim 13, wherein the square waves have a frequency of approximately two hundred kilohertz (kHz).

15. The system of claim 10, wherein the means for isolating the voltage comprises:
    means for generating an AC voltage from a DC voltage;
    means for rectifying a second DC voltage from the AC voltage; and
    means for receiving the second DC voltage from the rectifier.

16. The system of claim 10, wherein the biomedical signal comprises spectral content having a frequency between approximately one hertz (Hz) and approximately five hundred Hz.

* * * * *